(12) United States Patent
Taniyama et al.

(10) Patent No.: US 12,277,678 B2
(45) Date of Patent: Apr. 15, 2025

(54) MEDICAL IMAGE PROCESSING APPARATUS, X-ray DIAGNOSTIC APPARATUS, AND METHOD OF MEDICAL IMAGE PROCESSING

(71) Applicant: CANON MEDICAL SYSTEMS CORPORATION, Tochigi (JP)

(72) Inventors: Kazuhiro Taniyama, Otawara (JP); Hisato Takemoto, Nasushiobara (JP); Yoshiyasu Hayashi, Nasushiobara (JP); Tomoki Fujito, Nasushiobara (JP); Hirona Oikawa, Nasushiobara (JP); Yuya Suzuki, Nasushiobara (JP); Kenji Mizutani, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 79 days.

(21) Appl. No.: 17/654,669

(22) Filed: Mar. 14, 2022

(65) Prior Publication Data
US 2022/0292655 A1 Sep. 15, 2022

(30) Foreign Application Priority Data

Mar. 15, 2021 (JP) .................................. 2021-041654
Mar. 2, 2022 (JP) .................................. 2022-031855

(51) Int. Cl.
  *G06K 9/00* (2022.01)
  *A61B 6/00* (2006.01)
  (Continued)

(52) U.S. Cl.
  CPC .............. *G06T 5/50* (2013.01); *A61B 6/5217* (2013.01); *A61B 8/463* (2013.01); *A61B 8/483* (2013.01);
  (Continued)

(58) Field of Classification Search
  CPC . G06T 2207/10116; G06T 2207/10136; G06T 7/70; G06T 2207/20092;
  (Continued)

(56) References Cited

U.S. PATENT DOCUMENTS

| 8,466,914 B2 * | 6/2013 | Vion | A61B 8/483 |
| | | | 345/592 |
| 10,238,361 B2 * | 3/2019 | Gogin | A61B 6/5247 |

(Continued)

FOREIGN PATENT DOCUMENTS

| JP | 6297289 B2 | 3/2018 | |
| WO | WO-2012137451 A2 * | 10/2012 | ........... A61B 5/0037 |

OTHER PUBLICATIONS

M. Tory, A. E. Kirkpatrick, M. S. Atkins and T. Moller, "Visualization task performance with 2D, 3D, and combination displays," in IEEE Transactions on Visualization and Computer Graphics, vol. 12, No. 1, pp. 2-13, Jan.-Feb. 2006, doi: 10.1109/TVCG.2006.17. (Year: 2006).*

(Continued)

*Primary Examiner* — Gregory A Morse
*Assistant Examiner* — Kevin M Coomber
(74) *Attorney, Agent, or Firm* — Oblon, McClelland, Maier & Neustadt, L.L.P.

(57) ABSTRACT

A medical image processing apparatus of an embodiment includes processing circuitry acquiring an X-ray image about a subject, acquiring an ultrasonic image data about the subject, extracting an object contained in the X-ray image, and performing processing based on the position of the extracted object on the ultrasonic image data in accordance with the relative positional relation between a coordinate system in the X-ray image and a coordinate system in the ultrasonic image data to generate a composite image as a (Continued)

combination of a processed ultrasonic image data after being subjected to the processing and the X-ray image.

18 Claims, 9 Drawing Sheets

(51) Int. Cl.
  *A61B 8/00* (2006.01)
  *G06T 5/50* (2006.01)
  *G06T 7/70* (2017.01)
(52) U.S. Cl.
  CPC .............. *A61B 8/5261* (2013.01); *G06T 7/70* (2017.01); *G06T 2207/10116* (2013.01); *G06T 2207/10136* (2013.01); *G06T 2207/20092* (2013.01); *G06T 2207/20212* (2013.01); *G06T 2207/30004* (2013.01)
(58) Field of Classification Search
  CPC ............. G06T 2207/30004; G06T 5/50; G06T 2207/20212; A61B 6/5217; A61B 8/463; A61B 8/483; A61B 8/5261
  See application file for complete search history.

(56) References Cited

U.S. PATENT DOCUMENTS

| | | | |
|---|---|---|---|
| 2012/0245458 A1* | 9/2012 | Gogin ................. | A61B 6/5247 |
| | | | 600/424 |
| 2014/0037177 A1 | 2/2014 | Endo et al. | |
| 2015/0070385 A1* | 3/2015 | Ishizu .................... | A61B 6/502 |
| | | | 345/632 |
| 2015/0193931 A1* | 7/2015 | Fuchigami ............. | A61B 8/466 |
| | | | 382/132 |
| 2015/0193962 A1 | 7/2015 | Ohuchi et al. | |
| 2016/0030008 A1* | 2/2016 | Gerard ..................... | G06T 7/30 |
| | | | 600/440 |
| 2017/0186200 A1* | 6/2017 | Utsunomiya ........... | G06T 11/60 |
| 2018/0092537 A1 | 4/2018 | Endo et al. | |

OTHER PUBLICATIONS

Extended European Search Report issued Jul. 15, 2022 in European Patent Application No. 22162142.8, 7 pages.
Office Action issued May 24, 2024, in European Patent Application No. 22 162 142.8, filed Mar. 15, 2022, 3 pages.

* cited by examiner

X-RAY APPLICATION DIRECTION (IMAGE OBSERVATION DIRECTION)

FIG.6
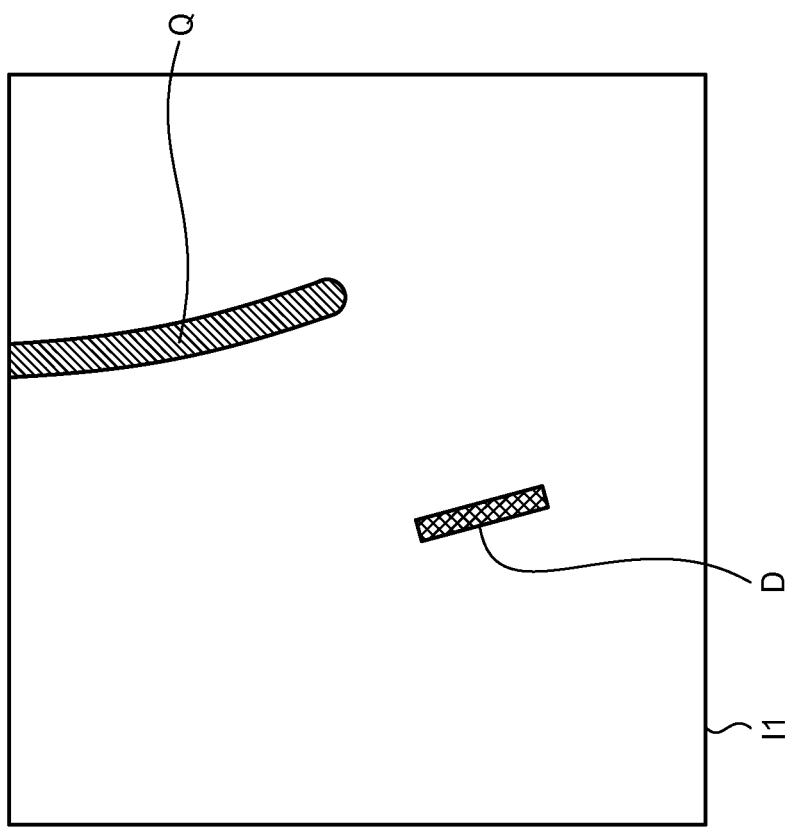
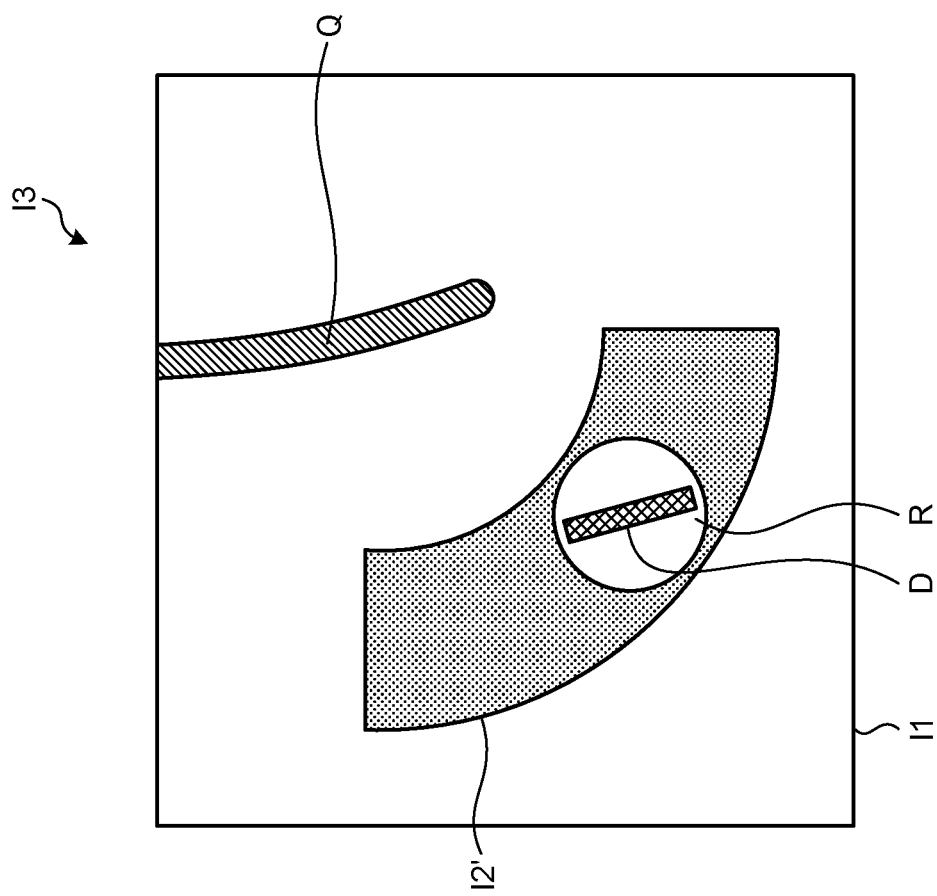

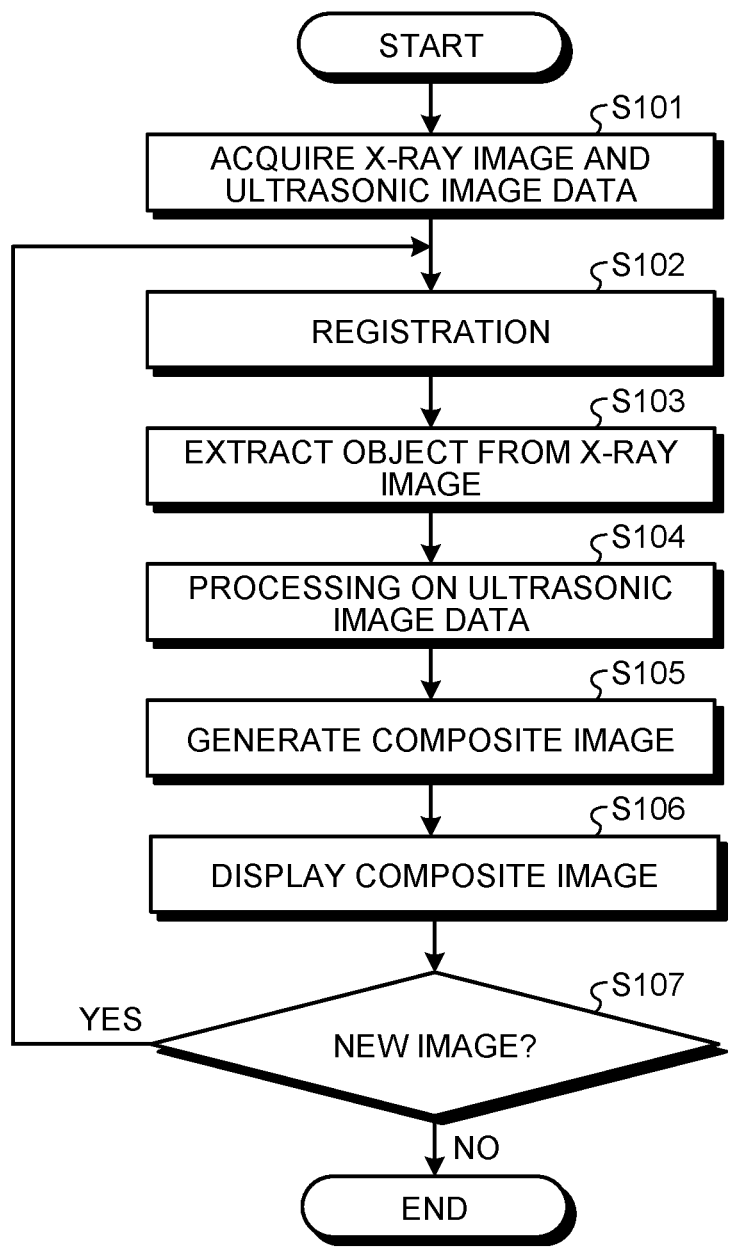

MEDICAL IMAGE PROCESSING APPARATUS, X-ray DIAGNOSTIC APPARATUS, AND METHOD OF MEDICAL IMAGE PROCESSING

CROSS-REFERENCE TO RELATED APPLICATIONS

This application is based upon and claims the benefit of priority from Japanese Patent Application No. 2021-041654, filed on Mar. 15, 2021; and Japanese Patent Application No. 2022-031855, filed on Mar. 2, 2022, the entire contents of which are incorporated herein by reference.

FIELD

Embodiments described herein relate generally to a medical image processing apparatus, an X-ray diagnostic apparatus, and a method of medical image processing.

BACKGROUND

Various methods of treatment performed by inserting a medical device into the body of a subject are known. When such treatment is performed, by acquiring and displaying an X-ray image of the subject, operation of the medical device by a surgeon can be supported. That is to say, by referring to the X-ray image, the surgeon can smoothly proceed with a procedure while grasping the positional relation between a region to be treated and the medical device within the body of the subject.

However, in the X-ray image, some structures such as soft tissues, for example, are difficult to appear on the image. Given this, by displaying another type of medical image such as an ultrasonic image and the X-ray image in a combined manner, more information can be provided to the surgeon.

BRIEF DESCRIPTION OF THE DRAWINGS

FIG. 6 is a diagram of a display example according to the first embodiment;

FIG. 7 is a flowchart for illustrating the sequence of processing by a medical image processing apparatus according to the first embodiment;

DETAILED DESCRIPTION

The following describes embodiments of a medical information processing apparatus, a medical information processing system, and a method of medical information processing in detail with reference to the accompanying drawings.

The following describes embodiments of a medical image processing apparatus, an X-ray diagnostic apparatus, and a method of medical image processing in detail with reference to the accompanying drawings.

Figure 1:
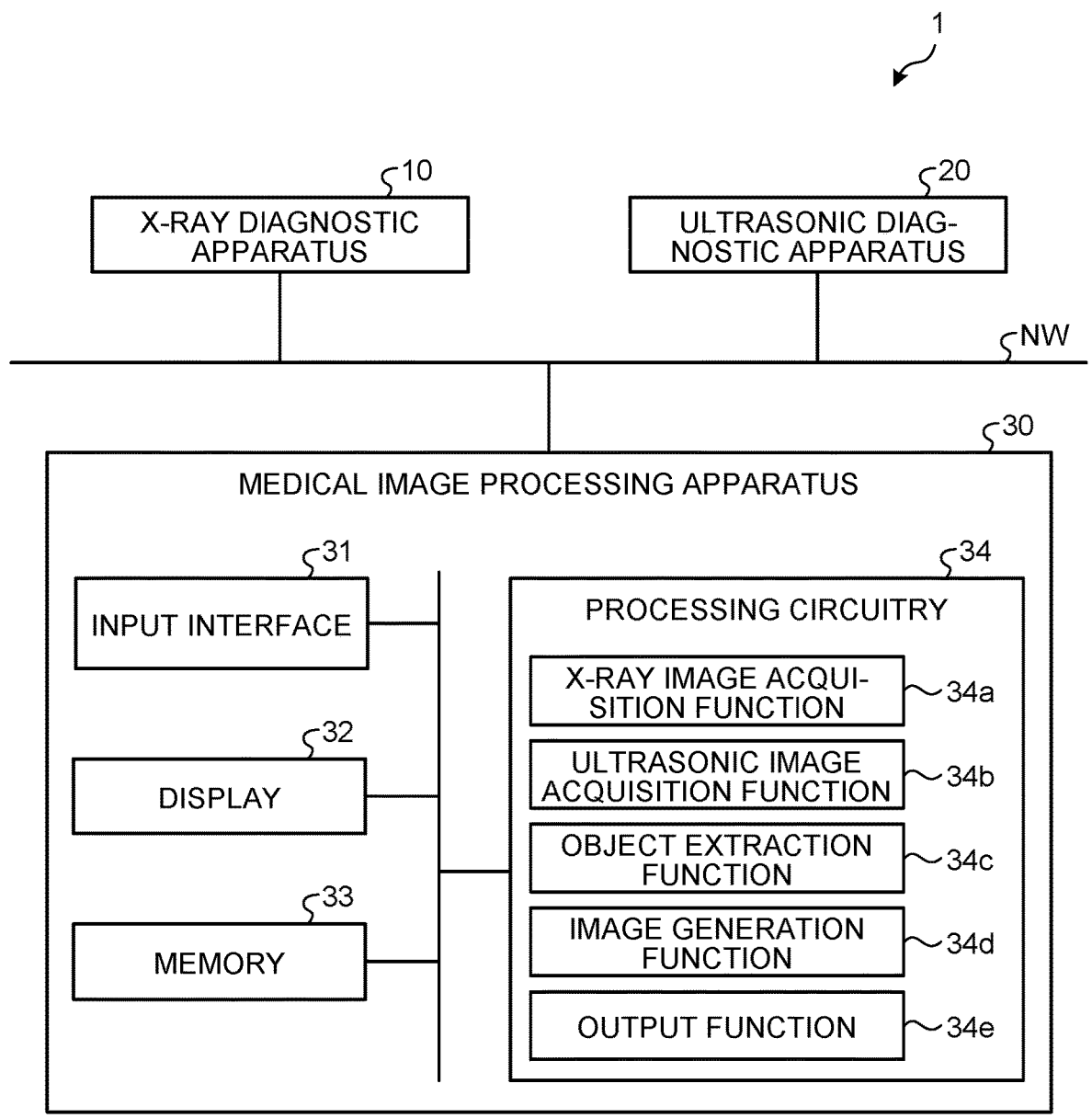
FIG. 1 is a block diagram of an example of the configuration of a medical image processing system according to a first embodiment.

A first embodiment describes a medical image processing system 1 including a medical image processing apparatus 30. FIG. 1 is a block diagram of an example of the configuration of the medical image processing system 1 according to the first embodiment. As illustrated in FIG. 1, the medical image processing system 1 according to the first embodiment includes an X-ray diagnostic apparatus 10, an ultrasonic diagnostic apparatus 20, and a medical image processing apparatus 30.

As illustrated in FIG. 1, the X-ray diagnostic apparatus 10, the ultrasonic diagnostic apparatus 20, and the medical image processing apparatus 30 are connected to each other via a network NW. So long as they can be connected to each other via the network NW, the X-ray diagnostic apparatus 10, the ultrasonic diagnostic apparatus 20, and the medical image processing apparatus 30 can be installed at any locations. The medical image processing apparatus 30 may be installed in a different hospital or another facility from that of the X-ray diagnostic apparatus 10 and the ultrasonic diagnostic apparatus 20, for example. That is to say, the network NW may include a local network closed within a hospital or be a network via the Internet.

The X-ray diagnostic apparatus 10 is an apparatus acquiring an X-ray image about a subject P. The X-ray diagnostic apparatus 10 acquires and displays the X-ray image while a procedure on the subject P is being performed, for example. To give an example, in cardiovascular treatment of structural cardiac diseases such as mitral valve repair, septal defect closure, and aortic valve repair, a surgeon inserts a medical device such as a catheter into the body of the subject P and operates it. The X-ray diagnostic apparatus 10 can acquire the X-ray image about the medical device inserted into the body of the subject P, a region to be treated within the body of the subject P, or the like and display it on a display.

Figure 2:
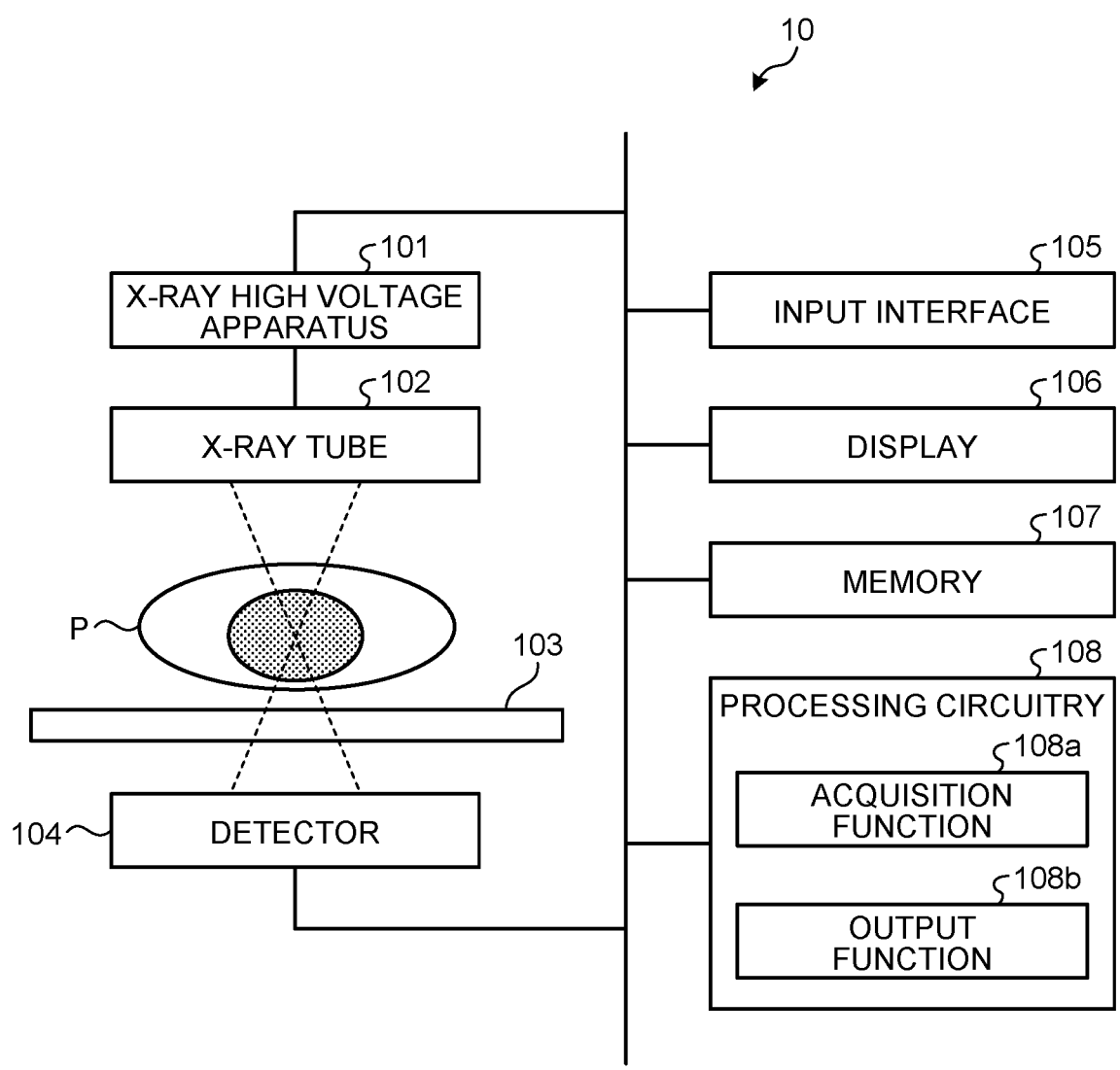
FIG. 2 is a block diagram of an example of the configuration of an X-ray diagnostic apparatus according to the first embodiment.

The following describes an example of the X-ray diagnostic apparatus 10 with reference to FIG. 2. FIG. 2 is a block diagram of an example of the configuration of the X-ray diagnostic apparatus 10 according to the first embodiment. As illustrated in FIG. 2, the X-ray diagnostic apparatus 10 includes an X-ray high voltage apparatus 101, an X-ray tube 102, a couchtop 103, a detector 104, an input interface 105, a display 106, a memory 107, and processing circuitry 108.

The X-ray high voltage apparatus 101 supplies high voltage to the X-ray tube 102 under the control of the processing circuitry 108. The X-ray high voltage apparatus 101 has an electric circuit such as a transformer and a rectifier and has a high voltage generation apparatus generating high voltage to be applied to the X-ray tube 102 and an X-ray control apparatus controlling output voltage corresponding to X-rays to be applied by the X-ray tube 102, for example. The high voltage generation apparatus may be of the transformer system or of the inverter system.

The X-ray tube 102 is a vacuum tube having a cathode (filament) generating thermoelectrons and an anode (target) generating X-rays upon collision with the thermoelectrons. The X-ray tube 102 applies the thermoelectrons from the cathode toward the anode using the high voltage supplied from the X-ray high voltage apparatus 101 to generate X-rays. Although omitted in FIG. 2, the X-ray diagnostic apparatus 10 may include an X-ray aperture near the X-ray application port of the X-ray tube 102. The X-ray aperture includes a collimator narrowing the application range of the X-rays generated by the X-ray tube 102 and a filter adjusting the X-rays emitted from the X-ray tube 102, for example.

The couchtop 103 is a bed on which the subject P is placed and is placed on a bed apparatus not illustrated. The subject P is not included in the X-ray diagnostic apparatus 10. The bed apparatus has a drive mechanism such as a motor and an actuator and controls the couchtop 103 by operating the drive mechanism under control of the processing circuitry 108 described below, for example. The bed apparatus adds drive voltage to the drive mechanism in accordance with a control signal received from the processing circuitry 108 to translate or tilt the couchtop 103, for example.

The detector 104 is an X-ray flat panel detector (FPD) having detector elements arranged in a matrix, for example. The detector 104 detects the X-rays emitted from the X-ray tube 102 and having passed through the subject P and outputs a detection signal corresponding to a detected X-ray dose to the processing circuitry 108. The detector 104 may be an indirect conversion type detector having a grid, a scintillator array, and an optical sensor array or a direct conversion type detector having a semiconductor element converting incident X-rays into an electric signal.

The detector 104 may be placed at a certain position under the couchtop 103 or be configured to be movable. The X-ray tube 102 and the detector 104 may be held by separate supports or be held integrally by a support such as a C-arm. Although FIG. 2 illustrates an overtube type configuration, in which the X-ray tube 102 is positioned above the subject P, the X-ray diagnostic apparatus 10 may be configured as an undertube type, in which the X-ray tube 102 is positioned below the subject P.

The input interface 105 receives various kinds of input operations from a user such as the surgeon, converts the received input operations into electric signals, and outputs them to the processing circuitry 108. The input interface 105 can be implemented by a mouse, a keyboard, a trackball, a switch, a button, a joystick, a touchpad performing input operations through touching on an operating surface, a touchscreen with a display screen and a touchpad integrated, a non-contact input circuit including an optical sensor, or a voice input circuit, for example. The input interface 105 may include a tablet terminal or the like that can wirelessly communicate with the X-ray diagnostic apparatus 10 main body. The input interface 105 may be a circuit receiving input operations from the user through motion capture. To give an example, by processing signals acquired via a tracker and images acquired about the user, the input interface 105 can receive user's body movements, gaze, and the like as input operations. The input interface 105 is not limited to those including physical operating components such as a mouse or a keyboard. Examples of the input interface 105 include an electric signal processing circuitry receiving electric signals corresponding to input operations from an external input device provided separately from the X-ray diagnostic apparatus 10 and outputting these electric signals to the processing circuitry 108.

The display 106 displays various kinds of information. The display 106 displays a graphical user interface (GUI) for receiving user instructions and medical images such as X-ray images under the control of the processing circuitry 108, for example. The display 106 is a liquid crystal display or a cathode ray tube (CRT) display, for example. The display 106 may be of a desktop type or include a tablet terminal or the like that can wirelessly communicate with the processing circuitry 108.

The memory 107 is implemented by a semiconductor memory element such as a random access memory (RAM) or a flash memory, a hard disk, or an optical disc, for example. The memory 107 stores therein various kinds of medical images such as X-ray images and computer programs corresponding to various functions to be read and executed by the processing circuitry 108, for example.

The processing circuitry 108 executes an acquisition function 108a and an output function 108b to control the operation of the entire X-ray diagnostic apparatus 10.

The processing circuitry 108 reads a computer program corresponding to the acquisition function 108a from the memory 107 and executes it to acquire the X-ray image about the subject P, for example. The acquisition function 108a is an example of a acquisition unit. The acquisition function 108a controls the X-ray high voltage apparatus 101 and adjusts the voltage to be supplied to the X-ray tube 102 to control an X-ray dose to be applied to the subject P and on and off, for example. The acquisition function 108a controls the operation of an imaging system including the X-ray tube 102 and the couchtop 103 to control an imaging range and an imaging angle. The acquisition function 108a generates an X-ray image based on the detection signal received from the detector 104. The acquisition function 108a may perform various kinds of image processing on the generated X-ray image. The acquisition function 108a executes noise reduction processing with an image processing filter and scattered ray correction on the generated X-ray image, for example.

The processing circuitry 108 reads a computer program corresponding to the output function 108b from the memory 107 and executes it to output the X-ray image acquired by the acquisition function 108a, for example. The output function 108b displays the X-ray image on the display 106, for example. The output function 108b transmits the X-ray image to an external apparatus via the network NW, for example. To give an example, the output function 108b transmits the X-ray image to the medical image processing apparatus 30. To give another example, the output function 108b transmits the X-ray image to an image storage apparatus not illustrated. The image storage apparatus is a server of a picture archiving and communication system (PACS), for example.

In the X-ray diagnostic apparatus 10 illustrated in FIG. 2, each processing function is stored in the memory 107 in the form of a computer program that can be executed by a computer. The processing circuitry 108 is a processor reading the computer program from the memory 107 and executing it to implement the function corresponding to each computer program. In other words, the processing circuitry 108 having read the computer program has the function corresponding to the read computer program.

Although the above in FIG. 2 describes a case in which the single processing circuitry 108 implements the acquisition function 108a and the output function 108b, a plurality of independent processors may be combined with each other to form the processing circuitry 108, and each of the processors may execute the computer program to implement the function. Each processing function of the processing circuitry 108 may be implemented by being distributed or integrated into a single circuit or a plurality of processing circuits as appropriate.

Referring back to FIG. 1, the description is continued. The ultrasonic diagnostic apparatus 20 illustrated in FIG. 1 is an apparatus acquiring ultrasonic image data about the subject P. The ultrasonic diagnostic apparatus 20 transmits and receives an ultrasonic wave using an ultrasonic probe while the procedure on the subject P is being performed to acquire the ultrasonic image data, for example. The ultrasonic image data acquired by the ultrasonic diagnostic apparatus 20 is combined with the X-ray image acquired by the X-ray diagnostic apparatus 10. A composite image of the X-ray image and the ultrasonic image data will be described below.

The ultrasonic probe included in the ultrasonic diagnostic apparatus 20 is adjusted in the position and orientation with respect to the subject P so that the medical device inserted into the body of the subject P, the region to be treated within the body of the subject P, and the like are contained in the imaging range, for example. The type of the ultrasonic probe is not limited to a particular one. The ultrasonic probe may be an intracorporeal probe such as a transesophageal echocardiography (TEE) probe or a body surface probe to be attached to the body surface of the subject P, for example.

The ultrasonic probe included in the ultrasonic diagnostic apparatus 20 has a plurality of transducer elements (piezoelectric transducer elements, for example), for example. The ultrasonic diagnostic apparatus 20 vibrates these transducer elements to generate an ultrasonic wave. The transducer elements receive a reflected wave from the subject P and convert it into an electric signal. That is to say, when the ultrasonic wave is transmitted to the subject P, the transmitted ultrasonic wave is reflected one after another by an acoustic impedance discontinuous surface in the body tissue of the subject P and is received by the transducer elements of the ultrasonic probe as a reflected wave signal (an echo signal). The amplitude of the received reflected wave signal depends on the difference in acoustic impedance at the discontinuous surface in which the ultrasonic wave is reflected. The reflected wave signal when the transmitted ultrasonic pulse is reflected by a moving bloodstream or a surface such as the heart wall undergoes a frequency shift depending on the velocity component of a moving object with respect to an ultrasonic transmission direction due to the Doppler effect.

The ultrasonic probe included in the ultrasonic diagnostic apparatus 20 may be a one-dimensional ultrasonic probe in which a plurality of piezoelectric transducer elements are arranged in a row, a one-dimensional ultrasonic probe in which a plurality of piezoelectric transducer elements arranged in a row are mechanically oscillated, or a two-dimensional ultrasonic probe in which a plurality of piezoelectric transducer elements are arranged in two dimensions in a grid shape.

Further, the ultrasonic diagnostic apparatus 20 generates ultrasonic image data based on the reflected wave signal received by the ultrasonic probe. The ultrasonic diagnostic apparatus 20 has a preamplifier, an analog/digital (A/D) converter, a reception delay unit, an adder, and the like and performs various kinds of processing on the reflected wave signal received by the ultrasonic probe to generate reflected wave data, for example. The ultrasonic diagnostic apparatus 20 controls the transmission direction of an ultrasonic beam from the ultrasonic probe to scan a three-dimensional region of the subject P and generates three-dimensional reflected wave data from the reflected wave signal received by the ultrasonic probe, for example.

The ultrasonic diagnostic apparatus 20 generates ultrasonic image data based on the reflected wave data and transmits the ultrasonic image data to the medical image processing apparatus 30. The type of the ultrasonic image data is not limited to a particular one and may be a B mode image or a Doppler image, for example. By performing logarithmic amplification, envelope detection processing, or the like on the reflected wave data, the ultrasonic diagnostic apparatus 20 can generate the B mode image, in which signal intensity for each sampling point is expressed in terms of the brightness of luminance, for example. By extracting motion information based on the Doppler effect of the moving object at each sampling point within a scanning region based on the reflected wave data, the ultrasonic diagnostic apparatus 20 can generate the Doppler image.

As illustrated in FIG. 1, for example, the medical image processing apparatus 30 has an input interface 31, a display 32, a memory 33, and processing circuitry 34.

The input interface 31, the display 32, and the memory 33 can be configured in the same manner as the input interface 105, the display 106, and the memory 107, respectively, described above. The input interface 31 receives various kinds of input operations from the user, converts the received input operations into electric signals, and outputs them to the processing circuitry 34, for example. The display 32, under the control of the processing circuitry 34, displays a GUI for receiving user instructions and various kinds of medical images such as X-ray images, ultrasonic image data, or composite images of these. The memory 33 stores therein various kinds of medical images such as X-ray images, ultrasonic image data, or composite images of these and stores therein computer programs corresponding to various kinds of functions read and executed by the processing circuitry 34.

The processing circuitry 34 executes an X-ray image acquisition function 34a, an ultrasonic image acquisition function 34b, an object extraction function 34c, an image generation function 34d, and an output function 34e to control the operation of the entire medical image processing apparatus 30. The X-ray image acquisition function 34a is an example of an X-ray image acquisition unit. The ultrasonic image acquisition function 34b is an example of an ultrasonic image acquisition unit. The object extraction function 34c is an example of an object extraction unit. The image generation function 34d is an example of an image generation unit. The output function 34e is an example of an output unit.

The processing circuitry 34 reads a computer program corresponding to the X-ray image acquisition function 34a from the memory 33 and executes it to acquire the X-ray image about the subject P, for example. The X-ray diagnostic apparatus 10 applies X-rays from the X-ray tube 102 to the subject P and detects the X-rays having passed through the subject P with the detector 104 to acquire the X-ray image, for example. The X-ray image acquisition function 34a acquires the X-ray image acquired by the X-ray diagnostic apparatus 10 via the network NW. The X-ray image acquisition function 34a may acquire the X-ray image directly from the X-ray diagnostic apparatus 10 or acquire it via another apparatus such as an image storage apparatus.

The processing circuitry 34 reads a computer program corresponding to the ultrasonic image acquisition function 34b from the memory 33 and executes it to acquire the ultrasonic image data about the subject P, for example. The ultrasonic diagnostic apparatus 20 controls the transmission and reception of the ultrasonic wave using the ultrasonic probe to acquire the ultrasonic image data, for example. The ultrasonic image acquisition function 34b acquires the ultrasonic image data acquired by the ultrasonic diagnostic apparatus 20 via the network NW. The ultrasonic image acquisition function 34b may acquire the ultrasonic image data directly from the ultrasonic diagnostic apparatus 20 or acquire it via another apparatus such as an image storage apparatus.

The processing circuitry 34 reads a computer program corresponding to the object extraction function 34c from the memory 33 and executes it to extract an object contained in an X-ray image, for example. The processing circuitry 34 reads a computer program corresponding to the image generation function 34d from the memory 33 and executes it to perform processing based on the position of the extracted object on the ultrasonic image data in accordance with the relative positional relation between a coordinate system in the X-ray image and a coordinate system in the ultrasonic image data and generates a composite image as a combination of processed ultrasonic image data after being subjected to the processing and the X-ray image, for example. The processing circuitry 34 reads a computer program corresponding to the output function 34e from the memory 33 and executes it to output the composite image generated by the image generation function 34d, for example. Processing by the object extraction function 34c the image generation function 34d, and the output function 34e will be described below.

In the medical image processing apparatus 30 illustrated in FIG. 1, each processing function is stored in the memory 33 in the form of a computer program that can be executed by a computer. The processing circuitry 34 is a processor reading the computer program from the memory 33 and executing it to implement the function corresponding to each computer program. In other words, the processing circuitry 34 having read each computer program has the function corresponding to the read computer program.

Although the above in FIG. 1 describes a case in which the single processing circuitry 34 implements the X-ray image acquisition function 34a, the ultrasonic image acquisition function 34b, the object extraction function 34c, the image generation function 34d, and the output function 34e, a plurality of independent processors may be combined with each other to form the processing circuitry 34, and each of the processors may execute the computer program to implement the function. Each processing function of the processing circuitry 34 may be implemented by being distributed or integrated into a single circuit or a plurality of processing circuitries as appropriate.

The above has described a configuration example of the medical image processing system 1. Under such a configuration, the medical image processing unit 30 in the medical image processing system 1 improves the visibility of the object contained in the X-ray image in the composite image of the X-ray image and the ultrasonic image data by processing by the processing circuitry 34.

Figure 3A:
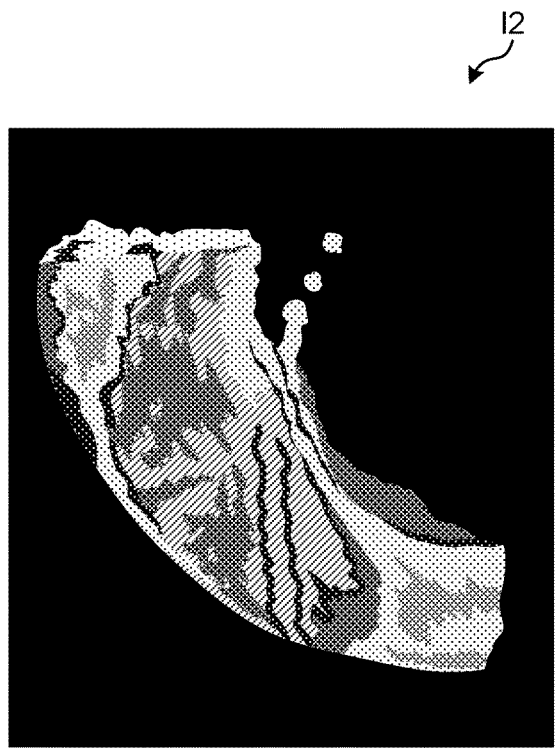
FIG. 3A is a diagram of an example of ultrasonic image data according to the first embodiment.

The following first describes a series of processing to generate and display the composite image of the X-ray image and the ultrasonic image data. After a procedure such as cardiovascular treatment is started, the X-ray diagnostic apparatus 10 acquires the X-ray image from the subject P, whereas the ultrasonic diagnostic apparatus 20 acquires the ultrasonic image data from the subject P, for example. The following describes a case in which the X-ray diagnostic apparatus 10 acquires an X-ray image I1 as an example. The X-ray image I1 is a two-dimensional image having two axes orthogonal to an X-ray application direction. The following describes a case in which the ultrasonic diagnostic apparatus 20 acquires ultrasonic image data I2 as an example. As illustrated in FIG. 3A for example, the ultrasonic image data I2 is a three-dimensional image data (volume data). FIG. 3A is a diagram of an example of the ultrasonic image data I2 according to the first embodiment.

The X-ray image acquisition function 34a acquires the X-ray image I1 acquired by the X-ray diagnostic apparatus 10 via the network NW. The ultrasonic image acquisition function 34b acquires the ultrasonic image data I2 acquired by the ultrasonic diagnostic apparatus 20 via the network NW. Next, the image generation function 34d generates a composite image of the X-ray image I1 and the ultrasonic image data I2.

Specifically, the image generation function 34d first identifies the relative positional relation between a coordinate system in the X-ray image I1 and a coordinate system in the ultrasonic image data I2. In other words, the image generation function 34d conducts registration process between the X-ray image I1 and the ultrasonic image data I2.

Figure 3B:
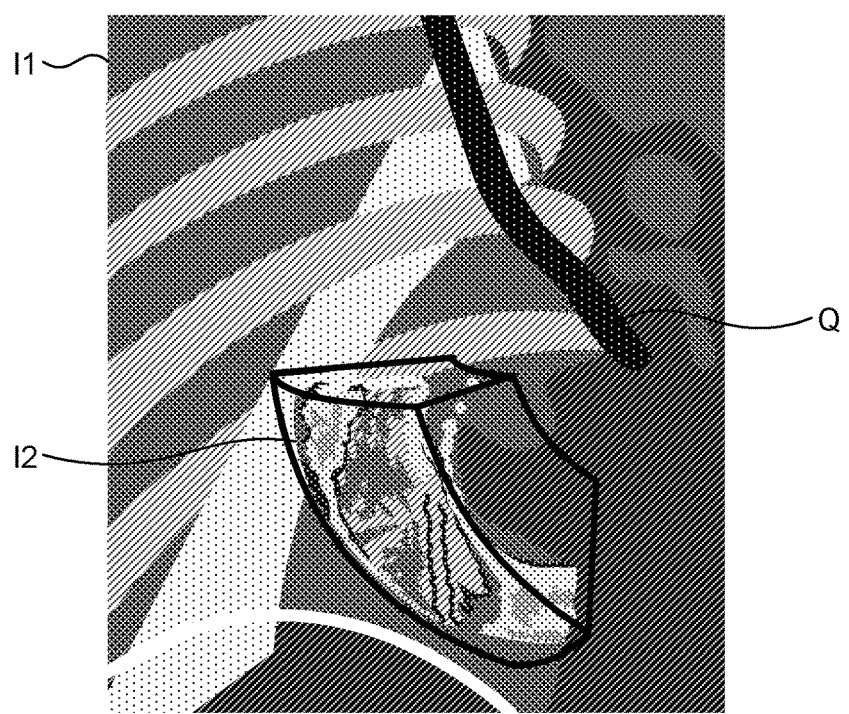
FIG. 3B is a diagram for illustrating generation processing for a composite image according to the first embodiment.

The image generation function 34d extracts an ultrasonic probe Q used to acquire the ultrasonic image data I2 from the X-ray image I1 to identify the relative positional relation between the coordinate system in the X-ray image I1 and the coordinate system in the ultrasonic image data I2, for example. That is to say, depending on the placement of the ultrasonic probe Q, the ultrasonic probe Q may be contained in the imaging range of the X-ray image I1 as illustrated in FIG. 3B. The image generation function 34d analyzes the X-ray image I1 and identifies the position and orientation of the ultrasonic probe Q to identify the relative positional relation between the coordinate system in the X-ray image I1 and the coordinate system in the ultrasonic image data I2. FIG. 3B is a diagram for illustrating generation processing for the composite image according to the first embodiment.

To give an example, the image generation function 34d extracts the ultrasonic probe Q from the X-ray image I1 using a three-dimensional model showing the ultrasonic probe Q. The three-dimensional model showing the ultrasonic probe Q can be generated from a three-dimensional image data imaging the ultrasonic probe Q, for example. To give an example, the three-dimensional model showing the ultrasonic probe Q can be generated from an X-ray computed tomography (CT) image (volume data) imaging the ultrasonic probe Q by an X-ray CT apparatus. Alternatively, the three-dimensional model showing the ultrasonic probe Q may be computer-aided design (CAD) data.

The image generation function 34d matches the three-dimensional model showing the ultrasonic probe Q to the X-ray image I1 to identify the position and orientation of the ultrasonic probe Q in the coordinate system of the X-ray image I1. By virtually projecting the three-dimensional model showing the ultrasonic probe Q onto a plane, the image generation function 34d can associate any position and orientation of the ultrasonic probe Q and the coordinate system of the X-ray image I1 with each other for each projection direction, for example. The projection direction (the X-ray application direction) at the time of acquiring the X-ray image I1 is known from the support angle of the X-ray diagnostic apparatus 10 or the like. By matching the three-dimensional model showing the ultrasonic probe Q to the X-ray image I1, the image generation function 34d can identify the position and orientation of the ultrasonic probe Q at the time of acquiring the X-ray image I1.

At the time of taking the ultrasonic image data I2, the ultrasonic diagnostic apparatus 20 transmits an ultrasonic beam from the transducer elements of the ultrasonic probe Q. In addition, the ultrasonic diagnostic apparatus 20 controls the transmission direction of the ultrasonic beam in accordance with an imaging condition to scan the three-dimensional region of the subject P. The ultrasonic image data I2 is generated for this three-dimensional scanning region, and thus the position and orientation of the ultrasonic image data I2 with respect to the ultrasonic probe Q are clear from the imaging condition. Consequently, by identifying the position and orientation of the ultrasonic probe Q in the coordinate system of the X-ray image I1, the image generation function 34d can identify the relative positional relation between the coordinate system in the X-ray image I1 and the coordinate system in the ultrasonic image data I2.

Although the above describes a case of identifying the relative positional relation between the coordinate system in the X-ray image I1 and the coordinate system in the ultrasonic image data I2 by extracting the ultrasonic probe Q from the X-ray image I1, the embodiment is not limited to this example. That is to say, the method for identifying the relative positional relation between the coordinate system in the X-ray image I1 and the coordinate system in the ultrasonic image data I2 is not limited to a particular method, and any method can be adopted.

When X-ray-opaque markers are attached to the ultrasonic probe Q, for example, the image generation function 34d may extract these markers from the X-ray image I1. Such markers are clearly depicted on the X-ray image I1, and thus they can be located easily and accurately. When three markers are attached, for example, the image generation function 34d can identify the position and orientation of the ultrasonic probe Q in the coordinate system of the X-ray image I1 based on the positions of the markers with respect to the ultrasonic probe Q and the distance between the markers on the X-ray image I1. The X-ray-opaque markers may be attached to a fixture (such as a belt) for attaching the ultrasonic probe Q to the subject P.

To give another example, when a sensor is attached to the ultrasonic probe Q, by detecting the position and orientation of the ultrasonic probe Q in the coordinate system of the X-ray image I1 with the sensor, the image generation function 34d can identify the relative positional relation between the coordinate system in the X-ray image I1 and the coordinate system in the ultrasonic image data I2. The sensor may be attached to the fixture for attaching the ultrasonic probe Q to the subject P.

After identifying the relative positional relation between the coordinate system in the X-ray image I1 and the coordinate system in the ultrasonic image data I2, the image generation function 34d can generate the composite image of the X-ray image I1 and the ultrasonic image data I2 in accordance with the identified positional relation. The image generation function 34d displays the ultrasonic image data I2 at a corresponding position on the X-ray image I1 in a superimposed manner as illustrated in FIG. 3B, for example. When the ultrasonic image data I2 is three-dimensional image data (volume data), for example, the image generation function 34d performs rendering processing in the X-ray application direction when the X-ray image I1 has been acquired to generate a two-dimensional ultrasonic image and generates a composite image of the two-dimensional ultrasonic image and the X-ray image I1.

The output function 34e displays the generated composite image on the display 32. Alternatively, the output function 34e may transmit the generated composite image to another apparatus, and the composite image may be displayed on the other apparatus. The output function 34e transmits the generated composite image to the X-ray diagnostic apparatus 10, for example. In this case, the output function 108b can display the composite image on the display 106.

By referring to the composite image of the X-ray image I1 and the ultrasonic image data I2, the user can efficiently grasp the position and shape of the medical device inserted into the body of the subject P, blood vessels contrasted by a contrast medium, soft tissues, and the like. However, as illustrated in FIG. 3B, in the composite image, the ultrasonic image data I2 overlaps with part of the X-ray image I1. Consequently, when the object such as the medical device operated by the user appears in the X-ray image I1, the object may be hidden by the ultrasonic image data I2. Given this, when generating the composite image of the X-ray image I1 and the ultrasonic image data I2, the medical image processing apparatus 30 further performs the following processing to improve the visibility of the object contained in the X-ray image I1.

Specifically, after the X-ray image acquisition function 34a acquires the X-ray image I1, the object extraction function 34c extracts the object contained in the X-ray image I1. The object is an object that the user focuses on, for example. Specific examples of the object include the medical device operated by the user, a blood vessel in the travel direction of the medical device, and the region to be treated. The object may be preset or be selected by the user as appropriate.

The method for extracting the object from the X-ray image I1 is not limited to a particular method. When the medical device such as a guidewire, a catheter, or a stent is used as the object, for example, by performing matching processing based on the shape of the medical device, the object extraction function 34c can extract the object contained in the X-ray image I1. The object extraction function 34c can also extract the object by methods such as thresholding and machine learning, for example. Alternatively, the object extraction function 34c may extract the object by receiving an operation to designate the object from the user having referred to the X-ray image I1.

Next, the image generation function 34d performs processing based on the position of the extracted object on the ultrasonic image data I2 in accordance with the relative positional relation between the coordinate system in the X-ray image I1 and the coordinate system in the ultrasonic image data I2. The image generation function 34d changes the transmittance of a region corresponding to the position of the extracted object out of the ultrasonic image data I2, for example.

The image generation function 34d first sets a region R for the ultrasonic image data I2 in accordance with the position of the object extracted in the X-ray image I1, for example. Specifically, the X-ray image I1 is a two-dimensional image having two axes orthogonal to the X-ray application direction, and the position of the object can be identified as two-dimensional coordinates. Thus, the image generation function 34d sets an axis passing through the coordinates corresponding to the position of the object and parallel to the X-ray application direction and sets the region R so as to contain the set axis.

Figure 4:
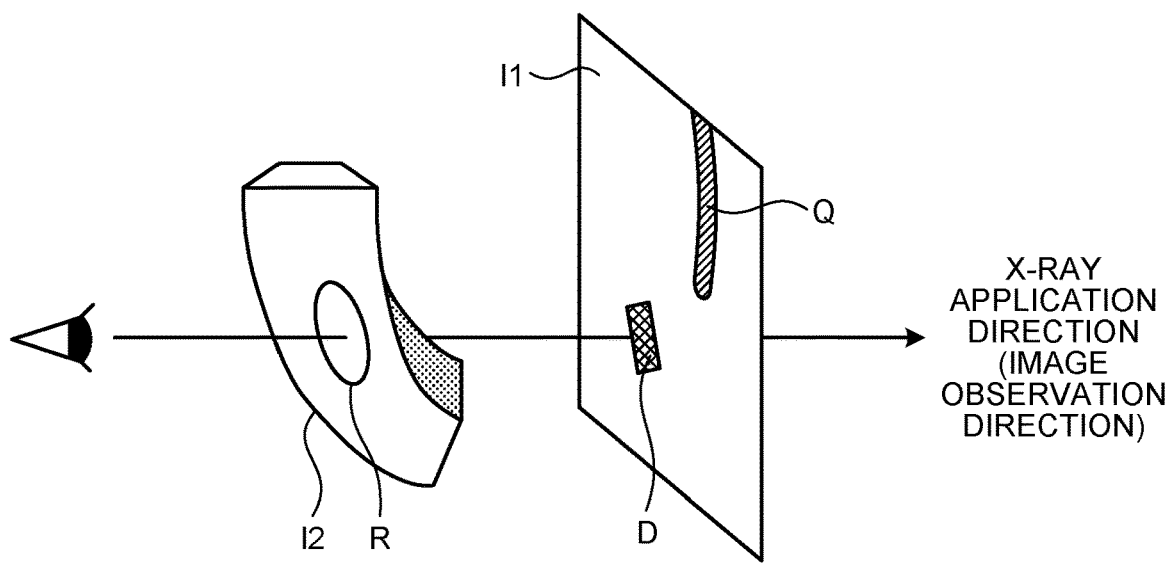
FIG. 4 is a diagram for illustrating processing on the ultrasonic image data according to the first embodiment.

The object extraction function 34c extracts an object D contained in the X-ray image as illustrated in FIG. 4, for example. FIG. 4 illustrates a case in which the object D is a stent as an example. Next, the image generation function 34d sets the region R so as to be circular when viewed from the X-ray application direction (an image observation direction) for the ultrasonic image data I2 in accordance with the position of the object D. Specifically, the image generation function 34d sets an axis passing through the coordinates corresponding to the position of object D and parallel to the X-ray application direction and defines a cylinder in which the set axis passes through the center of the bottom face thereof and the axis and the height direction thereof are parallel to each other. The image generation function 34d then sets a region in which the defined cylinder and the ultrasonic image data I2 overlap with each other as the region R. FIG. 4 is a diagram for illustrating the processing on the ultrasonic image data I2 according to the first embodiment.

After setting the region R, the image generation function 34d executes the processing on the ultrasonic image data I2. The image generation function 34d hides the region R, for example. In other words, the image generation function 34d changes the transmittance of the region R to "100%". The ultrasonic image data I2 after being subjected to the processing based on the position of the object D is also referred to as processed ultrasonic image data I2'.

Figure 5:
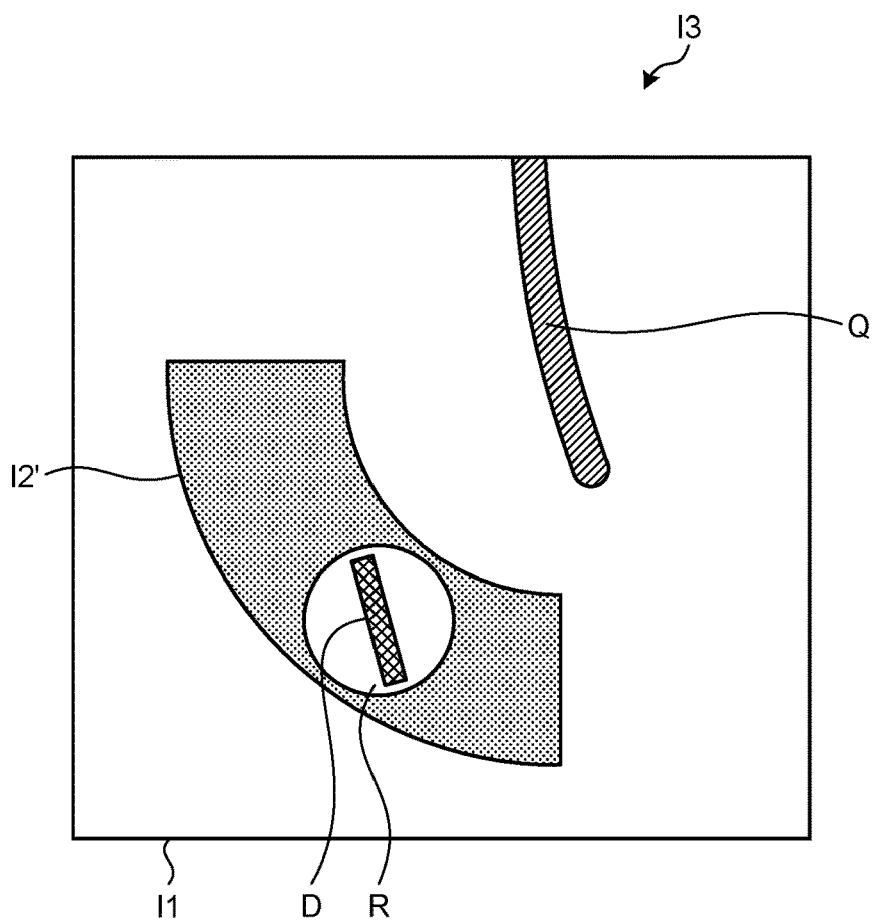
FIG. 5 is a diagram of an example of the composite image according to the first embodiment.

The image generation function 34d then generates a composite image I3 as a combination of the processed ultrasonic image data I2' and the X-ray image I1 as illustrated in FIG. 5. The image generation function 34d performs rendering processing in the X-ray application direction on the processed ultrasonic image data I2' to generate a two-dimensional ultrasonic image and then combines the two-dimensional ultrasonic image and the X-ray image I1 with each other to generate the composite image I3, for example. The type of the rendering processing is not limited to particular processing; an example is volume rendering (VR) processing, which generates a two-dimensional image reflecting three-dimensional information from volume data. FIG. 5 is a diagram of an example of the composite image according to the first embodiment.

The output function 34e displays the composite image I3 on the display 32. Alternatively, the output function 34e may transmit the composite image I3 to another apparatus, and the composite image I3 may be displayed on the other apparatus. The output function 34e transmits the generated composite image I3 to the X-ray diagnostic apparatus 10, for example. In this case, the output function 108b can display the composite image I3 on the display 106.

By referring to the composite image I3, the user can efficiently grasp the position and shape of the medical device inserted into the body of the subject P, blood vessels contrasted by a contrast medium, soft tissues, and the like. In the case illustrated in FIG. 5 in particular, although the position of the object D, which is a stent, and the imaging range of the ultrasonic image data I2 overlap with each other, the user can also visually recognize the object D because part of the ultrasonic image data I2 is hidden. That is to say, the medical image processing apparatus 30 can improve the visibility of the object D contained in the X-ray image I1 in the composite image I3 of the X-ray image I1 and the ultrasonic image data I2.

Although the region R of the ultrasonic image data I2 is hidden in FIG. 5, the displaying/hiding of the region R may be switchable. The output function 34e displays the composite image I3 on the display 32 and switches the displaying/hiding of the region R in accordance with an input operation from the user, for example. To give an example, the user operates a pointing device such as a mouse. The output function 34e can then switch the displaying/hiding of the region R with the composite image I3 being clicked with a mouse cursor or a certain button on the UI being pressed as a trigger.

Although the above in FIG. 5 describes a case of displaying the composite image I3 as a combination of the processed ultrasonic image data I2' and the X-ray image I1, the X-ray image I1 may further be displayed together with the composite image I3. The output function 34e displays the composite image I3 and the X-ray image I1 side by side as illustrated in FIG. 6, for example. With this configuration, the visibility of the object D can further be improved. That is to say, although in the composite image I3, the region R is hidden, so that the object D can be visually recognized, the surrounding area of the object D is hidden by the processed ultrasonic image data I2'. With the display example in FIG. 6, the object D can be observed including the surrounding area.

In addition, the output function 34e can display the composite image I3 together with various images. The output function 34e may display the composite image I3 and the ultrasonic image data I2 without the region R side by side, for example. The output function 34e may display the composite image I3, the X-ray image I1, and the ultrasonic image data I2 without the region R side by side, for example.

Although the above in FIG. 4 and FIG. 5 describes a case in which the region R is circular when viewed from the X-ray application direction, the shape of the region R can be changed as desired. The image generation function 34d may define a columnar region having a base shaped as desired and set a region in which the defined cylinder and the ultrasonic image data I2 overlap with each other as the region R, for example. To give an example, the image generation function 34d may define a columnar region having a base corresponding to the shape of the object D and set a region in which the defined columnar region and the ultrasonic image data I2 overlap with each other as the region R. That is to say, the image generation function 34d may perform processing based on the position and shape of the object D on the ultrasonic image data I2.

In addition, the shape of the region R can be changed in various ways. The image generation function 34d may define a columnar region having a height direction not parallel to the X-ray application direction and set a region in which the defined columnar region and the ultrasonic image data I2 overlap with each other as the region R, for example. Alternatively, the image generation function 34d may make the region R a non-columnar shape. The image generation function 34d may set a spherical or spindle-shaped region as the region R, for example.

Although the above in FIG. 4 and FIG. 5 describes a case of hiding the region R, the image generation function 34d may make the region R semi-transparent. The image generation function 34d may change the transmittance of the region R in the ultrasonic image data I2 to any value from "0°" to "100%", for example. The user may be allowed to change the transmittance in this case as desired. The image generation function 34d changes the region R in the ultrasonic image data I2 to a certain transmittance to generate the processed ultrasonic image data I2' and generates the composite image I3 as a combination of the processed ultrasonic image data I2' and the X-ray image I1, for example. The output function 34e displays the composite image I3 on the display 32 and changes the transmittance of the region R in accordance with an input operation from the user. To give an example, the user operates a pointing device such as a mouse. The output function 34e then changes the transmittance of the region R in accordance with the rotation of a mouse wheel or the operation of a certain bar on the UI.

The above in FIG. 4 describes a case in which the ultrasonic image data I2 is three-dimensional image data, and the region R is also set in three dimensions. However, embodiments are not limited to this example. The ultrasonic image data I2 may be a two-dimensional image, and the region R may be set in two dimensions, for example.

In this case, the ultrasonic image acquisition function 34b acquires the ultrasonic image data I2 as a two-dimensional image. The ultrasonic image acquisition function 34b acquires a three-dimensional ultrasonic image from the ultrasonic diagnostic apparatus 20 via the network NW and performs rendering processing in the X-ray application direction on the acquired three-dimensional ultrasonic image to acquire the two-dimensional ultrasonic image data I2, for example. Alternatively, the rendering processing can be performed in the ultrasonic diagnostic apparatus 20, and the ultrasonic image acquisition function 34b can acquire the two-dimensional ultrasonic image data I2 from the ultrasonic diagnostic apparatus 20 via the network NW. After the object D is extracted from the X-ray image I1 by the object extraction function 34c, the image generation function 34d sets a two-dimensional region corresponding to the position of the object D out of the two-dimensional ultrasonic image data I2 as the region R. The image generation function 34d changes the transmittance of the region R set in two dimensions to generate the processed ultrasonic image data I2'. That is to say, the image generation function 34d may change the transmittance of each voxel with the region R as a three-dimensional region or change the transmittance of each pixel with the region R as a two-dimensional region.

The following describes an example of the procedure of processing by the medical image processing apparatus 30 with reference to FIG. 7. FIG. 7 is a flowchart for illustrating the sequence of the processing by the medical image processing apparatus 30 according to the first embodiment. Step S101 and Step S107 correspond to the X-ray image acquisition function 34a and the ultrasonic image acquisition function 34b. Step S103 corresponds to the object extraction function 34c. Step S102, Step S104, and Step S105 correspond to the image generation function 34d. Step S106 corresponds to the output function 34e.

First, the processing circuitry 34 acquires the X-ray image I1 and the ultrasonic image data I2 (Step S101). Next, the processing circuitry 34 conducts registration process between the X-ray image I1 and the ultrasonic image data I2 (Step S102). That is to say, the processing circuitry 34 identifies the relative positional relation between the coordinate system in the X-ray image I1 and the coordinate system in the ultrasonic image data I2.

Next, the processing circuitry 34 extracts the object D from the X-ray image I1 (Step S103). Next, the processing circuitry 34 performs the processing based on the position of the extracted object D on the ultrasonic image data I2 in accordance with the relative positional relation between the coordinate system in the X-ray image I1 and the coordinate system in the ultrasonic image data I2 to generate the processed ultrasonic image data I2' (Step S104). Next, the processing circuitry 34 combines the X-ray image I1 and the processed ultrasonic image data I2' with each other to generate the composite image I3 (Step S105) and displays the generated composite image I3 on the display 32 (Step S106).

Next, the processing circuitry 34 determines the presence or absence of a new image (Step S107), and if there is a new image, it acquires the new image (affirmative at Step S107), and the process again moves to Step S102. That is to say, while the procedure on the subject P is being performed, the X-ray diagnostic apparatus 10 can repeatedly take the X-ray image I1 at a certain frame rate. Similarly, the ultrasonic diagnostic apparatus 20 can repeatedly take the ultrasonic image data I2 at a certain frame rate. In such a case, the processing circuitry 34 can successively acquire a new X-ray image I1 and a new ultrasonic image data I2, and if there is a new image, it can acquire the new image, again perform Step S102 to Step S106 based on the new image, and update the composite image I3 to be displayed in real time. On the other hand, if it is determined that there is no new image at Step S107 (negative at Step S107), the processing circuitry 34 ends the processing.

While the procedure on the subject P is being performed, the X-ray diagnostic apparatus 10 and the ultrasonic diagnostic apparatus 20 acquire the X-ray image I1 and the ultrasonic image data I2, respectively, in real time, for example. In this case, the processing circuitry 34, each time the X-ray image I1 is newly acquired from the subject P by the X-ray diagnostic apparatus 10, successively acquires the X-ray image I1 and, each time the ultrasonic image data I2 is newly acquired from the subject P by the ultrasonic diagnostic apparatus 20, successively acquires the ultrasonic image data I2. The processing circuitry 34 successively extracts the object D from the newly acquired X-ray image I1. The processing circuitry 34 successively performs the processing based on the position of the extracted object D on the newly acquired ultrasonic image data I2 and successively generates the composite image I3 as a combination of the processed ultrasonic image data I2' after being subjected to the processing and the newly acquired X-ray image I1. The processing circuitry 34 then successively displays the generated composite image I3 on the display 32. In this case, the composite image I3 displayed on the display 32 is a real-time image successively updated.

At Step S107, it may be determined that there is a new image when either the X-ray image I1 or the ultrasonic image data I2 is newly acquired. Assumed is a case in which the X-ray image I1 is acquired in real time, whereas the ultrasonic image data I2 is not acquired, for example. As the ultrasonic image data I2, not the real-time image but an image acquired before the start of the procedure, for example, can be used, for example. In such a case, by repeatedly executing the processing from Step S102 to Step S107, the processing circuitry 34 can successively update the part based on the X-ray image I1 out of the composite image I3 and display it in real time, although it cannot update the part based on the ultrasonic image data I2.

Alternatively, assumed is a case in which the ultrasonic image data I2 is acquired in real time, whereas the X-ray image I1 is not acquired. To give an example, a technique called last image hold (LIH) is known, in which an X-ray image lastly acquired is displayed in place of the real-time image, since exposure occurs while acquisition of X-ray images is continued. As the X-ray image I1, not the real-time image but LIH can be used. In such a case, by repeatedly executing the processing from Step S102 to Step S107, the processing circuitry 34 can successively update the part based on the ultrasonic image data I2 out of the composite image I3 and display it in real time, although it cannot update the part based on the X-ray image I1.

Although FIG. 7 illustrates a case in which the process moves to Step S102 when it is determined that there is a new image at Step S107, the process may move to Step S103 with Step S102 skipped. That is to say, even when at least either the X-ray image I1 or the ultrasonic image data I2 is newly acquired at Step S107, if there is no particular change in the imaging angle, the body movement of the subject P, or the like, the processing at Step S104 may be executed again in accordance with the positional relation identified in the past.

As described above, according to the first embodiment, the X-ray image acquisition function 34a acquires the X-ray image I1 about the subject P. The ultrasonic image acquisition function 34b acquires the ultrasonic image data I2 about the subject P. The object extraction function 34c extracts the object D contained in the X-ray image I1. The image generation function 34d performs the processing based on the position of the extracted object D on the ultrasonic image data I2 in accordance with the relative positional relation between the coordinate system in the X-ray image I1 and the coordinate system in the ultrasonic image data I2 and generates the composite image I3 as a combination of the processed ultrasonic image data I2' after being subjected to the processing and the X-ray image I1. Thus, the medical image processing apparatus 30 according to the first embodiment can improve the visibility of the object D contained in the X-ray image I1 in the composite image I3 of the X-ray image I1 and the ultrasonic image data I2.

The first embodiment described above describes a case in which setting of the region R is performed based on one X-ray image I1. In contrast, a second embodiment describes a case in which setting of the region R is performed based on a plurality of X-ray images I1. The medical image processing system 1 according to the second embodiment has the same configuration as that of the medical image processing system 1 illustrated in FIG. 1, with part of the processing by the image generation function 34d being different. Points having the same configuration as the configuration described in the first embodiment are denoted by the same signs as those in FIG. 1 and FIG. 2, and descriptions thereof are omitted.

The medical device such as a stent used in the treatment of cardiac diseases may fluctuate in position within the body of the subject P due to the influence of a heartbeat and the like, for example. When the X-ray images I1 of such a medical device are acquired over time, the position of the medical device on the X-ray images I1 changes for each cardiac phase.

The following describes a case in which setting of the region R is performed using the X-ray images I1 with reference to FIG. 8A, FIG. 8B, FIG. 9A, and FIG. 9B. The X-ray images I1 is X-ray images of a plurality of time phase acquired in time series. FIG. 8A, FIG. 8B, FIG. 9A, and FIG. 9B are diagrams of examples of region setting processing according to the second embodiment.

Figure 8A:
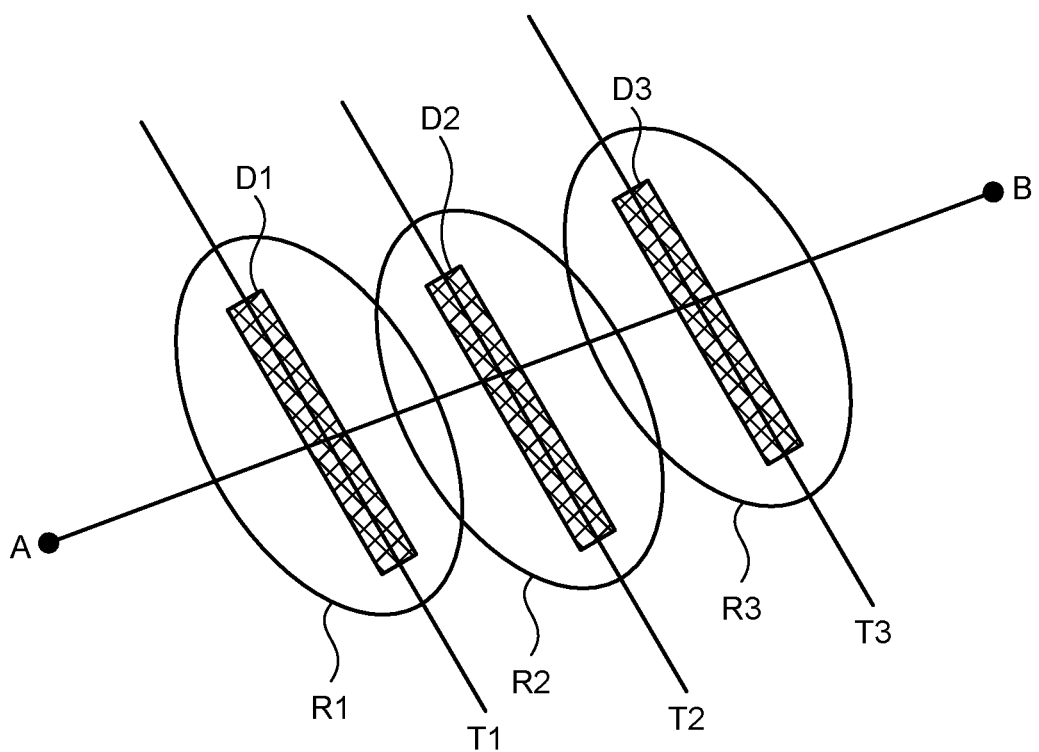
FIG. 8A is a diagram of an example of region setting processing according to a second embodiment.

The X-ray diagnostic apparatus 10 acquires an X-ray image at a time T1, acquires an X-ray image at a time T2, and acquires an X-ray image at a time T3, for example. The X-ray images acquired at times T1, T2, and T3 are examples of the X-ray image I1. In this case, as illustrated in FIG. 8A, the position of the medical device at the time T1 (hereinafter referred to as an object D1), the position of the medical device at the time T2 (hereinafter referred to as an object D2), and the position of the medical device at the time T3 (hereinafter referred to as an object D3) may be different from each other.

The object extraction function 34c extracts the object D1 contained in the X-ray image acquired at time T1, and the image generation function 34d sets a region R1 according to the position of the object D1 out of the ultrasonic image data I2. Similarly, the object extraction function 34c extracts the object D2 contained in the X-ray image acquired at time T2, and the image generation function 34d sets a region R2 according to the position of the object D2 out of the ultrasonic image data I2. Similarly, the object extraction function 34c extracts the object D3 contained in the X-ray image acquired at time T3, and the image generation function 34d sets a region R3 according to the position of the object D3 out of the ultrasonic image data I2. The regions R1 to R3 illustrated in FIG. 8A are elliptic regions based on the position and shape of the extracted object D.

The image generation function 34d can generate processed ultrasonic image data with the transmittance of the region R1 out of the ultrasonic image data I2 changed and generate a composite image as a combination of the processed ultrasonic image data and the X-ray image acquired at time T1. Similarly, the image generation function 34d can generate processed ultrasonic image data with the transmittance of the region R2 out of the ultrasonic image data I2 changed and generate a composite image as a combination of the processed ultrasonic image data and the X-ray image acquired at time T2. Similarly, the image generation function 34d can generate processed ultrasonic image data with the transmittance of the region R3 out of the ultrasonic image data I2 changed and generate a composite image as a combination of the processed ultrasonic image data and the X-ray image acquired at time T3.

However, when the composite image as a combination of the processed ultrasonic image data with the transmittance of the region R1 out of the ultrasonic image data I2 changed and the X-ray image acquired at time T1, the composite image as a combination of the processed ultrasonic image data with the transmittance of the region R2 out of the ultrasonic image data I2 changed and the X-ray image acquired at time T2, the composite image as a combination of the processed ultrasonic image data with the transmittance of the region R3 out of the ultrasonic image data I2 changed and the X-ray image acquired at time T3, and the like are successively displayed, the position of the region R with the transmittance changed successively moves, and the region R may be difficult to visually recognize. In addition, it is difficult to accurately extract the object D moving due to the influence of the heartbeat and the like from each of the X-ray images I1, and the tracking of the region R to be set may be insufficient.

Given these circumstances, the image generation function 34d sets the region R in accordance with a plurality of positions of the object D corresponding to the respective X-ray images I1. That is to say, the image generation function 34d does not set one region R from one X-ray image I1 but sets one region R from the X-ray images I1.

Figure 8B:
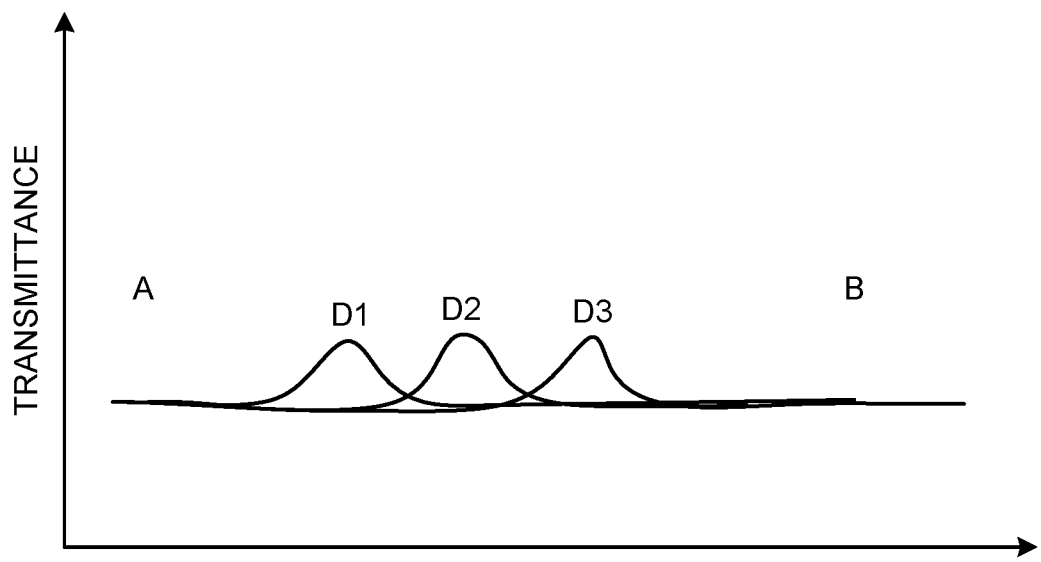
FIG. 8B is a diagram of an example of the region setting processing according to the second embodiment.

The image generation function 34d sets a single combined region as a combination of the regions R1 to R3 illustrated in FIG. 8A and changes the transmittance of the combined region, for example. The transmittance of each position in this combined region can be profiled as illustrated in FIG. 8B, for example. Specifically, the positions of the respective objects D1 to D3 are contained on the line segment A-B illustrated in FIG. 8A. The image generation function 34d profiles the transmittance such that the transmittance at the positions of the respective objects D1 to D3 is higher than that at other positions.

The image generation function 34d generates processed ultrasonic image data with the transmittance of each position of the ultrasonic image data I2 changed in accordance with the transmittance profile illustrated in FIG. 8B. The image generation function 34d also generates a composite image as a combination of the processed ultrasonic image data with the transmittance of each position of the ultrasonic image data I2 changed in accordance with the transmittance profile illustrated in FIG. 8B and the X-ray image acquired at time T1. The image generation function 34*d* also generates a composite image as a combination of the processed ultrasonic image data with the transmittance of each position of the ultrasonic image data I2 changed in accordance with the transmittance profile illustrated in FIG. 8B and the X-ray image acquired at time T2. The image generation function 34*d* also generates a composite image as a combination of the processed ultrasonic image data with the transmittance of each position of the ultrasonic image data I2 changed in accordance with the transmittance profile illustrated in FIG. 8B and the X-ray image acquired at time T3.

When the composite image as a combination of the processed ultrasonic image data with the transmittance of each position of the ultrasonic image data I2 changed in accordance with the transmittance profile illustrated in FIG. 8B and the X-ray image acquired at time T1, the composite image as a combination of the processed ultrasonic image data with the transmittance of each position of the ultrasonic image data I2 changed in accordance with the transmittance profile illustrated in FIG. 8B and the X-ray image acquired at time T2, the composite image as a combination of the processed ultrasonic image data with the transmittance of each position of the ultrasonic image data I2 changed in accordance with the transmittance profile illustrated in FIG. 8B and the X-ray image acquired at time T3, and the like are successively displayed, the position of the region R (the combined region of the regions R1 to R3) with the transmittance changed does not move, and no reduction in visibility occurs. Even if the extraction of the object D is inaccurate in any of the X-ray images I1, in many cases the object D will be contained in the region R. That is to say, in the case illustrated in FIG. 8A and FIG. 8B, even if the tracking of the moving object D is insufficient, a reduction in visibility can be inhibited.

Figure 9A:
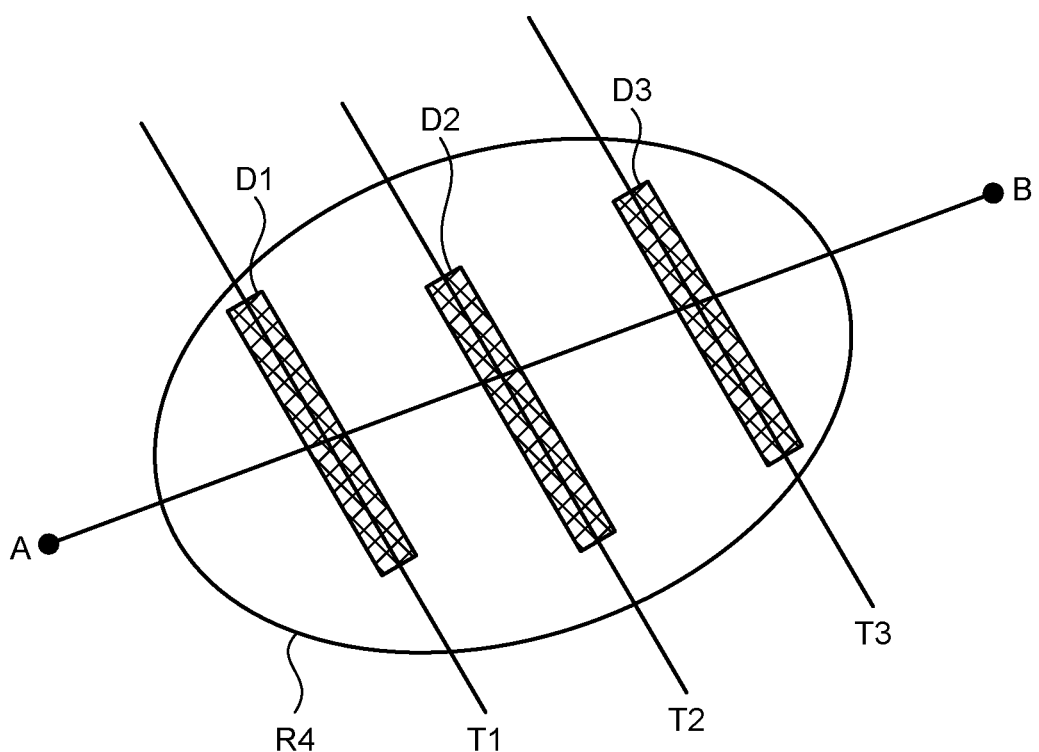
FIG. 9A is a diagram of an example of the region setting processing according to the second embodiment.
Figure 9B:
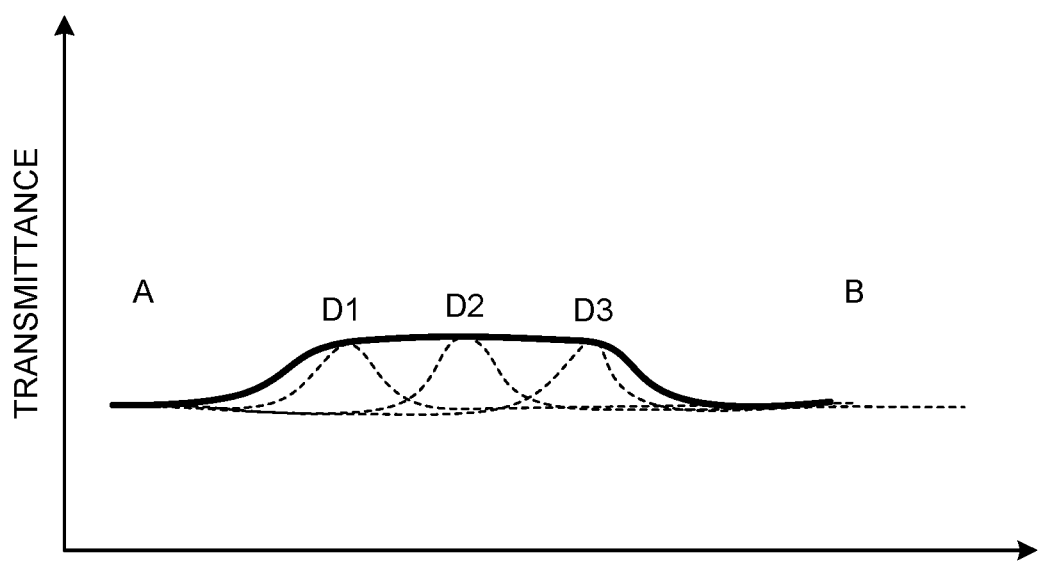
FIG. 9B is a diagram of an example of the region setting processing according to the second embodiment.

Alternatively, the image generation function 34*d* may set a single region R4 containing the objects D1 to D3 as illustrated in FIG. 9A. The transmittance of each position in the region R4 can be profiled as illustrated in FIG. 9B, for example. That is to say, the image generation function 34*d* profiles the transmittance for each position on the line segment A-B such that the transmittance in the region R4 is higher than that at other positions.

The image generation function 34*d* generates processed ultrasonic image data with the transmittance of each position of the ultrasonic image data I2 changed in accordance with the transmittance profile illustrated in FIG. 9B. The image generation function 34*d* also generates a composite image as a combination of the processed ultrasonic image data with the transmittance of each position of the ultrasonic image data I2 changed in accordance with the transmittance profile illustrated in FIG. 9B and the X-ray image acquired at time T1. The image generation function 34*d* also generates a composite image as a combination of the processed ultrasonic image data with the transmittance of each position of the ultrasonic image data I2 changed in accordance with the transmittance profile illustrated in FIG. 9B and the X-ray image acquired at time T2. The image generation function 34*d* also generates a composite image as a combination of the processed ultrasonic image data with the transmittance of each position of the ultrasonic image data I2 changed in accordance with the transmittance profile illustrated in FIG. 9B and the X-ray image acquired at time T3.

When the composite image as a combination of the processed ultrasonic image data with the transmittance of each position of the ultrasonic image data I2 changed in accordance with the transmittance profile illustrated in FIG. 9B and the X-ray image acquired at time T1, the composite image as a combination of the processed ultrasonic image data with the transmittance of each position of the ultrasonic image data I2 changed in accordance with the transmittance profile illustrated in FIG. 9B and the X-ray image acquired at time T2, the composite image as a combination of the processed ultrasonic image data with the transmittance of each position of the ultrasonic image data I2 changed in accordance with the transmittance profile illustrated in FIG. 9B and the X-ray image acquired at time T3, and the like are successively displayed, the position of the region R4 with the transmittance changed does not move, and no reduction in visibility occurs. Even if the extraction of the object D is inaccurate in any of the X-ray images I1, in many cases the object D will be contained in the region R4. That is to say, in the case illustrated in FIG. 9A and FIG. 9B, even if the tracking of the moving object D is insufficient, a reduction in visibility can be inhibited. In the case illustrated in FIG. 9A and FIG. 9B, the transmittance profile is smoother than that in the case illustrated in FIG. 8A and FIG. 8B, and thus the visibility of the object D can further be improved.

Although the above describes a case in which the region R is set from three X-ray images I1, the number of the X-ray images I1 used to set the region R can be changed as desired. The X-ray diagnostic apparatus 10 repeats the acquisition of the X-ray image I1 for a period corresponding to one heartbeat of the subject P at a certain frame rate, for example. In this case, the image generation function 34*d* can set the region R based on the X-ray images I1 corresponding to one heartbeat of the subject P. Alternatively, the image generation function 34*d* may set the region R based on the X-ray images I1 corresponding to a plurality of heartbeats of the subject P. Although the above describes a case in which the object D is influenced by the heartbeat, the same can be applied to a case in which the object D moves due to the breathing of subject P, for example.

The first and second embodiments have been described; various different forms may be performed other than the embodiments described above.

The embodiments described above describe a case in which the object D is the medical device such as a stent, for example. However, embodiments are not limited to this example. The same can be applied to a case in which a blood vessel, an organ, or the like of the subject P is selected as the object D, for example. Any other structures can be selected as the object D so long as they appear on the X-ray image.

The embodiments described above describe a case in which the processing on the ultrasonic image data I2 is performed based on the extraction result of the object D by the object extraction function 34*c* to generate the processed ultrasonic image data I2'. However, embodiments are not limited to this example. The image generation function 34*d* may perform processing based on an input operation from the user on the ultrasonic image data I2 to generate the processed ultrasonic image data I2', for example.

The image generation function 34*d* performs processing based on both the extraction result of the object D by the object extraction function 34*c* and the input operation from the user on the ultrasonic image data I2 to generate the processed ultrasonic image data I2', for example. To give an example, the image generation function 34*d* first sets the region R in the ultrasonic image data I2 in accordance with the position of the object extracted by the object extraction function 34*c*. The output function 34*e* displays the set region R on the display 32, and the image generation function 34*d* receives an operation to process the position and shape of the region R from the user. The image generation function 34d changes the transmittance of the region R after being processed based on the input operation from the user out of the ultrasonic image data I2 to generate the processed ultrasonic image data I2'.

The image generation function 34d receives an input operation from the user when the object D has not been extracted from the X-ray image I1, for example. The object extraction function 34c cannot necessarily recognize the object D due to image noise in the X-ray image I1 and the like, for example. In such a case, the output function 34e displays the X-ray image I1 on the display 32, and the image generation function 34d receives an operation to designate the position of the object D from the user. The image generation function 34d changes the transmittance of the region R corresponding to the position designated by the user out of the ultrasonic image data I2 to generate the processed ultrasonic image data I2'. Alternatively, the output function 34e displays the ultrasonic image data I2 on the display 32, and the image generation function 34d receives an operation to set the position and shape of the region R from the user. The image generation function 34d changes the transmittance of the region R set by the user out of the ultrasonic image data I2 to generate the processed ultrasonic image data I2'.

The embodiments described above describe a case in which the processing circuitry 34 of the medical image processing apparatus 30 executes the various kinds of functions such as the X-ray image acquisition function 34a, the ultrasonic image acquisition function 34b, the object extraction function 34c, the image generation function 34d, and the output function 34e. However, embodiments are not limited to this example. The processing circuitry 108 of the X-ray diagnostic apparatus 10 may execute functions corresponding to the functions of the processing circuitry 34, for example.

Figure 10:
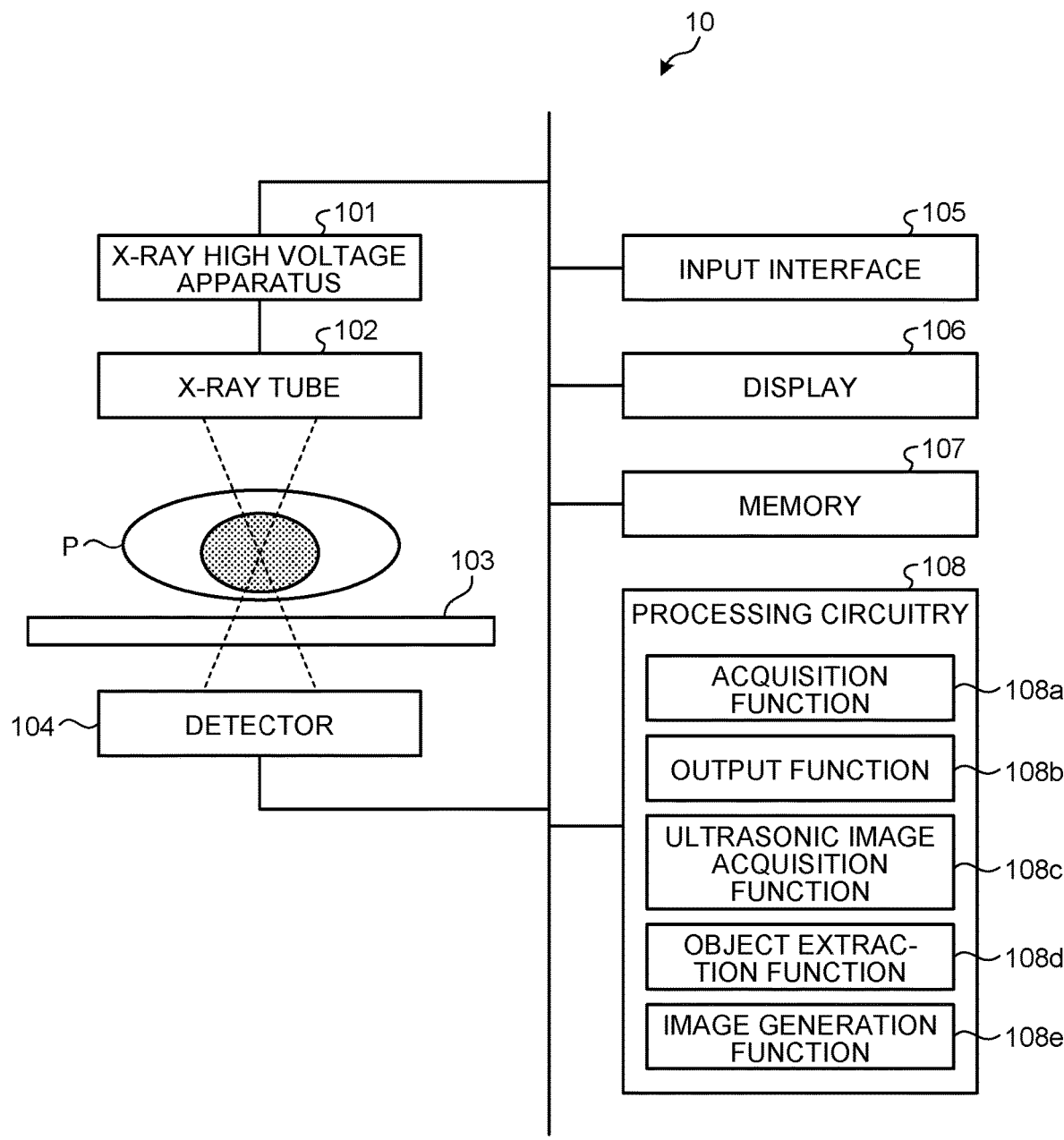
FIG. 10 is a block diagram of an example of the configuration of the X-ray diagnostic apparatus according to a third embodiment.

The following describes this point with reference to FIG. 10. FIG. 10 is a block diagram of an example of the configuration of the X-ray diagnostic apparatus 10 according to a third embodiment. The X-ray diagnostic apparatus 10 illustrated in FIG. 10 differs from the X-ray diagnostic apparatus 10 illustrated in FIG. 2 in that the processing circuitry 108 further has an ultrasonic image acquisition function 108c, an object extraction function 108d, and an image generation function 108e.

The ultrasonic image acquisition function 108c is a function corresponding to the ultrasonic image acquisition function 34b. The object extraction function 34c is a function corresponding to the object extraction function 108d. The image generation function 34d is a function corresponding to the image generation function 108e. The ultrasonic image acquisition function 34b is an example of the ultrasonic image acquisition unit. The object extraction function 34c is an example of the object extraction function unit. The image generation function 34d is an example of the image generation function unit.

The acquisition function 108a acquires the X-ray image I1 about the subject P, for example. The ultrasonic image acquisition function 34b acquires the ultrasonic image data I2 about the subject P via the network NW. The object extraction function 108d extracts the object D contained in the X-ray image I1. The image generation function 108e performs the processing based on the position of the extracted object D on the ultrasonic image data I2 in accordance with the relative positional relation between the coordinate system in the X-ray image I1 and the coordinate system in the ultrasonic image data I2 to generate the composite image I3 as a combination of the processed ultrasonic image data I2' after being subjected to the processing and the X-ray image I1. The output function 108b can display the generated composite image I3 on the display 106.

The term "processor" used in the above description means a circuit such as a CPU, a graphics processing unit (GPU), an application specific integrated circuit (ASIC), a programmable logic device (a simple programmable logic device (SPLD), a complex programmable logic device (CPLD), or a field programmable gate array (FPGA), for example), for example. When the processor is a CPU, for example, the processor reads a computer program stored in a memory and executes it to implement a function. On the other hand, when the processor is an ASIC, for example, in place of storing the computer program in the memory, the function is directly embedded in the circuitry of the processor as a logic circuit. Each processor of the embodiments is not limited to being configured as a single circuit for each processor but may also be configured as one processor by combining a plurality of independent circuits to implement its functions. Further, a plurality of components in each drawing may be integrated into one processor to implement their functions.

The above in FIG. 1 describes a case in which the single memory 33 stores therein the computer program corresponding to each processing function of the processing circuitry 34. The above in FIG. 2 and FIG. 10 describes a case in which the single memory 107 stores therein the computer program corresponding to each processing function of the processing circuitry 108. However, embodiments are not limited to this example. A plurality of memories 33 may be placed in a distributed manner, and the processing circuitry 34 may read from the individual memory 33 the corresponding computer program, for example. Similarly, a plurality of memories 107 may be placed in a distributed manner, and the processing circuitry 108 may read from the individual memory 107 the corresponding computer program. In place of storing the computer program in the memory 33 or the memory 107, the computer program may directly be embedded in the circuitry of the processor. In this case, the processor reads the computer program embedded in the circuitry and executes it to implement its function.

The components of each apparatus according to the embodiments described above are functionally conceptual ones and do not necessarily need to be physically configured as illustrated in the drawing. That is to say, the specific form of the dispersion and integration of each apparatus is not limited to the one illustrated in the drawing, but the whole or part thereof can be configured in a functionally or physically distributed and integrated manner in any unit in accordance with various kinds of loads, use conditions, and the like. Further, the whole or any part of the processing functions performed by each apparatus can be implemented by a CPU and a computer program that is analyzed and executed by the CPU or be implemented as hardware by wired logic.

The method of medical image processing described in the embodiments described above can be implemented by executing a computer program prepared in advance on a computer such as a personal computer or a workstation. This computer program can be distributed via a network such as the Internet. This computer program can also be executed by being recorded on a computer-readable, non-transitory recording medium such as a hard disk, flexible disk (FD), a compact disc read only memory (CD-ROM), magneto-optical (MO), or a digital versatile disc (DVD) and being read from the recording medium by a computer.

At least one of the embodiments described above can improve the visibility of the object contained in the X-ray image in the composite image of the X-ray image and the ultrasonic image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Note 1. A medical image processing apparatus comprising:
  an X-ray image acquisition unit configured to acquire an X-ray image about a subject;
  an ultrasonic image acquisition unit configured to acquire an ultrasonic image data about the subject;
  an object extraction unit configured to extract an object contained in the X-ray image; and
  an image generation unit configured to perform processing based on a position of the extracted object on the ultrasonic image data in accordance with a relative positional relation between a coordinate system in the X-ray image and a coordinate system in the ultrasonic image data to generate a composite image as a combination of a processed ultrasonic image data after being subjected to the processing and the X-ray image.

Note 2. The image generation unit may change transmittance of a region corresponding to the position of the object out of the ultrasonic image data as the processing.

Note 3. The processing based on a position of the extracted object may include increasing transmittance of a region corresponding to the position of the object out of the ultrasonic image data.

Note 4. The object may be an object that a user focuses on.

Note 5. The object may be a medical device operated by a user, a blood vessel in the travel direction of the medical device, or a region to be treated.

Note 6. The X-ray image acquisition unit may acquire X-ray images of a plurality of time phase,
  the object extraction unit may extract the object from each of the X-ray images, and
  the image generation unit may set the region in accordance with a plurality of positions of the object corresponding to the respective X-ray images to change the transmittance of the region.

Note 7. The ultrasonic image data may be a three-dimensional image data, and
  the image generation unit may change transmittance of a three-dimensional region corresponding to the position of the object out of the ultrasonic image data to generate the processed ultrasonic image data.

Note 8. The ultrasonic image data may be a two-dimensional image data, and
  the image generation unit may change transmittance of a two-dimensional region corresponding to the position of the object out of the ultrasonic image data to generate the processed ultrasonic image data.

Note 9. The X-ray image acquisition unit may, each time the X-ray image is newly acquired from the subject by an X-ray diagnostic apparatus, successively acquire the X-ray image, the ultrasonic image data acquisition unit may, each time the ultrasonic image data is newly acquired from the subject by an ultrasonic diagnostic apparatus, successively acquire the ultrasonic image data,
the object extraction unit may successively extract the object from the newly acquired X-ray image, and
the image generation unit may successively perform the processing on the newly acquired ultrasonic image data in accordance with the positional relation to successively generate the composite image as a combination of the processed ultrasonic image data after being subjected to the processing and the newly acquired X-ray image.

Note 10. The image generation unit may perform processing based on an input operation from a user on the ultrasonic image data to generate the processed ultrasonic image data.

Note 11. The image generation unit may changes the transmittance of the region corresponding to the position of the object in accordance with rotation of a mouse wheel or operation of a certain bar on an UI.

Note 12. The image generation unit may receive the input operation when the object has not been extracted from the X-ray image.

Note 13. The image generation unit may extract an ultrasonic probe used to acquire the ultrasonic image data from the X-ray image to identify the positional relation.

Note 14. The image generation unit may perform the processing based on a position and shape of the extracted object on the ultrasonic image data.

Note 15. An output unit configured to display the composite image and the X-ray image side by side may further be included.

Note 16. An X-ray diagnostic apparatus comprising:
  an acquisition unit configured to acquire an X-ray image about a subject;
  an ultrasonic image data acquisition unit configured to acquire an ultrasonic image data about the subject;
  an object extraction unit configured to extract an object contained in the X-ray image; and
  an image generation unit configured to perform processing based on a position of the extracted object on the ultrasonic image data in accordance with a relative positional relation between a coordinate system in the X-ray image and a coordinate system in the ultrasonic image data to generate a composite image as a combination of a processed ultrasonic image data after being subjected to the processing and the X-ray image.

Note 17. A computer program causing a computer to execute each component of the medical image processing apparatus.

Note 18. A method of medical image processing comprising:
  acquiring an X-ray image about a subject;
  acquiring an ultrasonic image data about the subject;
  extracting an object contained in the X-ray image; and
  performing processing based on a position of the extracted object on the ultrasonic image data in accordance with a relative positional relation between a coordinate system in the X-ray image and a coordinate system in the ultrasonic image data to generate a composite image as a combination of a processed ultrasonic image data after being subjected to the processing and the X-ray image.

Note 19. In the method of medical image processing, transmittance of a region corresponding to the position of the object out of the ultrasonic image data may be changed as the processing.

Note 20. The processing based on a position of the extracted object may include increasing transmittance of a region corresponding to the position of the object out of the ultrasonic image data.

Note 21. The object may be an object that a user focuses on.

Note 22. The object may be a medical device operated by a user, a blood vessel in the travel direction of the medical device, or a region to be treated.

Note 23. In the method of medical image processing,
X-ray images of a plurality of time phase may be acquired,
the object may be extracted from each of the X-ray images, and
the region may be set in accordance with a plurality of positions of the object corresponding to the respective X-ray images to change the transmittance of the region.

Note 24. In the method of medical image processing,
the ultrasonic image data may be a three-dimensional image data, and
transmittance of a three-dimensional region corresponding to the position of the object out of the ultrasonic image data may be changed to generate the processed ultrasonic image data.

Note 25. In the method of medical image processing,
The ultrasonic image data may be a two-dimensional image data, and
transmittance of a two-dimensional region corresponding to the position of the object out of the ultrasonic image data may be changed to generate the processed ultrasonic image data.

Note 26. In the method of medical image processing,
each time the X-ray image is newly acquired from the subject by an X-ray diagnostic apparatus, the X-ray image may successively be acquired,
each time the ultrasonic image data is newly acquired from the subject by an ultrasonic diagnostic apparatus, the ultrasonic image data may successively be acquired,
the object may successively be extracted from the newly acquired X-ray image, and
the processing may successively be performed on the newly acquired ultrasonic image data in accordance with the positional relation to successively generate the composite image as a combination of the processed ultrasonic image data after being subjected to the processing and the newly acquired X-ray image.

Note 27. In the method of medical image processing, processing based on an input operation from a user may be performed on the ultrasonic image data to generate the processed ultrasonic image data.

Note 28. In the method of medical image processing, the transmittance of the region corresponding to the position of the object may be changed in accordance with rotation of a mouse wheel or operation of a certain bar on an UI.

Note 29. In the method of medical image processing, the input operation may be received when the object has not been extracted from the X-ray image.

Note 30. The method of medical image processing according to claim 13, in the method of medical image processing, an ultrasonic probe used to acquire the ultrasonic image data is extracted from the X-ray image to identify the positional relation.

Note 31. In the method of medical image processing, the processing based on a position and shape of the extracted object may be performed on the ultrasonic image data.

Note 32. In the method of medical image processing, the composite image and the X-ray image may be displayed side by side.

What is claimed is:

1. A medical image processing apparatus, comprising: processing circuitry configured to acquire an X-ray image of a subject, acquire ultrasonic image data of the subject, extract a medical device contained in the acquired X-ray image, and perform processing based on a position of the extracted medical device in the ultrasonic image data in accordance with a relative positional relation between a coordinate system in the X-ray image and a coordinate system in the ultrasonic image data to generate a composite image as a combination of processed ultrasonic image data after being subjected to the processing and the X-ray image, wherein the processing circuitry is further configured to, as the processing, change a display parameter of a region containing the position of the extracted medical device in the ultrasonic image data so as to increase a transparency of the region.

2. The medical image processing apparatus according to claim 1, wherein the processing circuitry is further configured to
acquire X-ray images of a plurality of time phases,
extract the medical device from each of the acquired X-ray images, and
set the region in accordance with a plurality of positions of the medical device corresponding to the respective X-ray images to increase the transparency of the region.

3. The medical image processing apparatus according to claim 1, wherein
the ultrasonic image data is three-dimensional image data, and
the processing circuitry is further configured to increase the transparency of the region, which is a three-dimensional region corresponding to the position of the medical device in the ultrasonic image data, to generate the processed ultrasonic image data.

4. The medical image processing apparatus according to claim 1, wherein
the ultrasonic image data is two-dimensional image data, and
the processing circuitry is further configured to increase the transparency of the region, which is a two-dimensional region corresponding to the position of the medical device out of the ultrasonic image data to generate the processed ultrasonic image data.

5. The medical image processing apparatus according to claim 1, wherein the processing circuitry is further configured to:
each time the X-ray image is newly acquired from the subject by an X-ray diagnostic apparatus, successively acquire the X-ray image,
each time the ultrasonic image data is newly acquired from the subject by an ultrasonic diagnostic apparatus, successively acquire the ultrasonic image data,
successively extract the medical device from the newly acquired X-ray image, and
successively perform the processing on the newly acquired ultrasonic image data in accordance with the positional relation to successively generate the composite image as a combination of the processed ultrasonic image data after being subjected to the processing and the newly acquired X-ray image.

6. The medical image processing apparatus according to claim 1, wherein the processing circuitry is further configured to perform the processing, based on an input operation from a user, on the ultrasonic image data to generate the processed ultrasonic image data.

7. The medical image processing apparatus according to claim 6, wherein the processing circuitry is further configured to receive the input operation when the medical device has not been extracted from the X-ray image.

8. The medical image processing apparatus according to claim 1, wherein the processing circuitry is further configured to extract the medical device, which is an ultrasonic probe used to acquire the ultrasonic image, from the X-ray image to identify the positional relation.

9. The medical image processing apparatus according to claim 1, wherein the processing circuitry is further configured to perform the processing based on the position and a shape of the extracted medical device in the ultrasonic image data.

10. The medical image processing apparatus according to claim 1, wherein the processing circuitry is further configured to cause a display to display the composite image and the X-ray image side by side.

11. An X-ray diagnostic apparatus, comprising: an X-ray tube that generates X-rays; a detector that has detector elements; and processing circuitry configured to acquire an X-ray image of a subject, acquire ultrasonic image data of the subject, extract a medical device contained in the acquired X-ray image, and perform processing based on a position of the extracted medical device in the ultrasonic image data in accordance with a relative positional relation between a coordinate system in the X-ray image and a coordinate system in the ultrasonic image data to generate a composite image as a combination of a processed ultrasonic image data after being subjected to the processing and the X-ray image, wherein the processing circuitry is further configured to, as the processing, change a display parameter of a region containing the position of the extracted medical device in the ultrasonic image data so as to increase a transparency of the region.

12. A method of medical image processing, comprising: acquiring an X-ray image of a subject, acquiring ultrasonic image data of the subject, extracting a medical device contained in the acquired X-ray image, and performing processing based on a position of the extracted medical device on the ultrasonic image data in accordance with a relative positional relation between a coordinate system in the X-ray image and a coordinate system in the ultrasonic image data to generate a composite image as a combination of a processed ultrasonic image data after being subjected to the processing and the X-ray image, wherein the performing step further comprises changing a display parameter of a region containing the position of the extracted medical device in the ultrasonic image data so as to increase a transparency of the region.

13. The method of medical image processing according to claim 12, further comprising:
acquiring X-ray images of a plurality of time phases,
extracting the medical device from each of the acquired X-ray images, and
setting the region in accordance with a plurality of positions of the medical device corresponding to the respective X-ray images to increase the transparency of the region.

14. The method of medical image processing according to claim 13, wherein
the ultrasonic image data is three-dimensional image data, and
the method further comprises changing the transparency of the region, which is a three-dimensional region corresponding to the position of the medical device in the ultrasonic image data, to generate the processed ultrasonic image data.

15. The method of medical image processing according to claim 12, further comprising:
each time the X-ray image is newly acquired from the subject by an X-ray diagnostic apparatus, successively acquiring the X-ray image,
each time the ultrasonic image data is newly acquired from the subject by an ultrasonic diagnostic apparatus, successively acquiring the ultrasonic image data,
successively extracting the medical device from the newly acquired X-ray image, and
successively performing the processing on the newly acquired ultrasonic image data in accordance with the positional relation to successively generate the composite image as a combination of the processed ultrasonic image data after being subjected to the processing and the newly acquired X-ray image.

16. The method of medical image processing according to claim 12, wherein the extracting step further comprises extracting the medical device, which is an ultrasonic probe used to acquire the ultrasonic image data is extracted, from the X-ray image to identify the positional relation.

17. The method of medical image processing according to claim 12, wherein the step of performing the processing further comprises performing the processing based on the position and a shape of the extracted medical device in the ultrasonic image data.

18. The method of medical image processing according to claim 12, further comprising displaying the composite image and the X-ray image side by side.

* * * * *